United States Patent [19]
Slassi et al.

[11] Patent Number: 6,133,287
[45] Date of Patent: Oct. 17, 2000

[54] PIPERIDINE-INDOLE COMPOUNDS HAVING 5-HT$_6$ AFFINITY

[75] Inventors: Abdelmalik Slassi; Louise Edwards, both of Mississauga; Anne O'Brien, Toronto; Tao Xin, North York; Ashok Tehim, Mississauga, all of Canada

[73] Assignee: Allelix Biopharmaceuticals Inc., Ontario, Canada

[21] Appl. No.: 09/046,669

[22] Filed: Mar. 24, 1998

[51] Int. Cl.$^7$ ............... A61K 31/445; C07D 401/04
[52] U.S. Cl. ............... 514/318; 514/339; 546/201; 546/273.4
[58] Field of Search ............... 514/318, 339; 546/201, 273.4

[56] References Cited

U.S. PATENT DOCUMENTS

| | | | |
|---|---|---|---|
| 3,481,953 | 12/1969 | Herbst et al. | 548/468 |
| 3,489,429 | 1/1970 | Herbst et al. | 548/468 |
| 3,489,770 | 1/1970 | Herbst et al. | 548/468 |
| 4,021,431 | 5/1977 | Zenitz | 546/201 |
| 4,870,085 | 9/1989 | Glaser et al. | 514/323 |
| 5,066,660 | 11/1991 | Oxford et al. | 514/323 |
| 5,834,493 | 11/1998 | Gil-Guintero et al. | 514/339 |
| 5,846,982 | 12/1998 | Audia et al. | 514/318 |

FOREIGN PATENT DOCUMENTS

| | | |
|---|---|---|
| 0 815 861 | 6/1997 | European Pat. Off. |
| WO 94/14770 | 7/1994 | WIPO |

OTHER PUBLICATIONS

Scholl et al. "Selective serotonin reuptake nhibitors in treatment of . . . " Medline 95098179, 1995.
Amlaiky et al. "The mouse HT5 and 5HT6 receptors . . . " Biosis 87634, 1993.
Whitaker–Azmitia et al. "The neuropharmacology of serotonin" N. Y. Aca. Sci. v. 600, p. 168, 1990.
Taylor et al. Molecular determinants for recognition of RU 24969 nanlogs . . . ) Mol. Pharm. v.34, pp. 42–53, 1988.
Hansch et al. "The structure–activity relationship of inhibitors of serotonin uptake . . . " J. Computor aided mol. design. vol. 5, pp. 441–453, 1991.
Bundgaard "Design of prodrugs" Elsevier, p. 28–29, 1986.
Guillaume et al. "Synthesis of 3–(1,2,3, 6–tetrahydropyridin–4–yl)!Hindoles and study . . . " CA 107:70255, 1987.
Simpson et al. "Autoradiography with [3H]8–OH–DPAT reveals increases in 5HT1A . . . " CA 125:354432, 1996.
International Application No. WO 90/05721 published May 31, 1990.
International Application No. WO 92/13856 published Aug. 20, 1992.
International Application No. WO 95/32966 published Dec. 7, 1995.
International Application No. WO 96/25397 published Aug. 22, 1996.
International Application No. WO 97/47302 published Dec. 18, 1997.
Taylor et al., Molecular Pharmacology, vol. 34, 1988, pp. 42–53, "Molecular Determinants for Recogination of RU 24969 Analogs at Central 5–Hydroxytryptamine . . . ".
Zheng et al., Heterocycles, vol. 37, No. 3, 1994, "Vinylation of the indole 3–postion via palladium–catalyzed cross–coupling".
Zheng et al., Tetrahedron Letters, vol. 34, No. 14, pp. 2235–2238, 1993, "Palladium Catalyzed Cross–Coupling Reaction between 3–Indole Boronic Acids . . . ".
Japanese Abstract No. JP 05043544, Feb. 23, 1993.

*Primary Examiner*—Ceila Chang
*Attorney, Agent, or Firm*—Arent, Fox, Kintner, Plotkin & Kahn, PLLC

[57] ABSTRACT

Described herein are compounds with affinity for the 5-HT$_6$ receptor, which have the general formula:

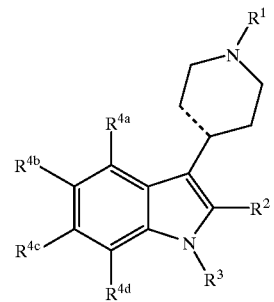

wherein:
  $R^1$ is selected from the group consisting of H and $C_{1-4}$alkyl;
  $R^2$ is selected from the group consisting of H, $C_{1-4}$alkyl and benzyl;
  — — — represents a single or double bond;
  $R^3$ is selected from the group consisting of $COR^5$ and $SO_2R^5$;
  $R^{4a}$ is selected from the group consisting of H, OH, halo, $C_{1-4}$alkyl and $C_{1-4}$alkoxy;
  $R^{4b}$ is selected from the group consisting of H, hydroxy, halo, $C_{3-7}$cycloalkyloxy, $C_{1-4}$alkoxy, $C_{1-4}$alkyl, benzyloxy, phenoxy, trifluoromethyl, trifluoromethoxy and vinyl;
  $R^{4c}$ is selected from the group consisting of H, OH, halo, $C_{1-4}$alkyl and $C_{1-4}$alkoxy;
  $R_{4d}$ is selected from the group consisting of H, OH, halo, $C_{1-4}$alkyl and $C_{1-4}$alkoxy; and
  $R^5$ is selected from the group consisting of phenyl, pyridyl, thienyl, quinolinyl and naphthyl which are optionally substituted with 1–4 substituents selected from $C_{1-4}$alkoxy, $C_{1-4}$alkyl, halo, nitro, trifluoromethyl, trifluoromethoxy, 1,2-methylenedioxy, $C_{1-4}$alkylcarbonyl, $C_{1-4}$alkoxycarbonyl and $C_{1-4}$alkylS—. Also described is the use of these compounds as pharmaceuticals to treat indications where inhibition of the 5-HT$_6$ receptor is implicated, such as schizophrenia.

19 Claims, No Drawings

PIPERIDINE-INDOLE COMPOUNDS HAVING 5-HT₆ AFFINITY

This invention relates to indole compounds having affinity for the serotonin 5-HT$_6$ receptor, to pharmaceutical compositions containing them and to their medical use, particularly in the treatment of CNS conditions.

According to one aspect of the invention, there are provided compounds of Formula I and salts, solvates or hydrates thereof:

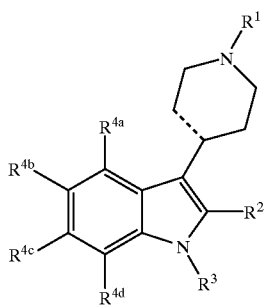

I wherein:
- $R^1$ is selected from the group consisting of H and $C_{1-4}$alkyl;
- $R^2$ is selected from the group consisting of H, $C_{1-4}$alkyl and benzyl;
- ----- represents a single or double bond;
- $R^3$ is selected from the group consisting of $COR^5$ and $SO_2R^5$;
- $R^{4a}$ is selected from the group consisting of H, OH, halo, $C_{1-4}$alkyl and $C_{1-4}$alkoxy;
- $R^{4b}$ is selected from the group consisting of H, hydroxy, halo, $C_{3-7}$cycloalkyloxy, $C_{1-4}$alkoxy, $C_{1-4}$alkyl, benzyloxy, phenoxy, trifluoromethyl, trifluoromethoxy and vinyl;
- $R^{4c}$ is selected from the group consisting of H, OH, halo, $C_{1-4}$alkyl and $C_{1-4}$alkoxy;
- $R^{4d}$ is selected from the group consisting of H, OH, halo, $C_{1-4}$alkyl and $C_{1-4}$alkoxy; and
- $R^5$ is selected from the group consisting of phenyl, pyridyl, thienyl, quinolinyl and naphthyl which are optionally substituted with 1–4 substituents selected from $C_{1-4}$alkoxy, $C_{1-4}$alkyl, halo, nitro, trifluoromethyl, trifluoromethoxy, 1,2-methylenedioxy, $C_{1-4}$alkylcarbonyl, $C_{1-4}$alkoxycarbonyl and $C_{1-4}$alkylS—.

According to another aspect of the invention, there is provided a pharmaceutical composition comprising a compound of Formula I in an amount effective to antagonize the 5-HT$_6$ receptor, and a pharmaceutically acceptable carrier.

In another aspect of the present invention there are provided compositions containing the present compounds in amounts for pharmaceutical use to treat CNS conditions where a 5-HT$_6$ ligand is indicated, for example, for the treatment or prevention of central nervous system disturbances such as psychosis, schizophrenia, manic depression, depression, neurological disturbances, memory disturbances, Parkinsonism, amylotrophic lateral sclerosis, Alzheimer's disease and Huntington's disease. These and other aspects of the present invention are described in greater detail hereinbelow.

DETAILED DESCRIPTION AND PREFERRED EMBODIMENTS

The term "$C_{1-4}$alkyl" as used herein means straight and branched chain alkyl radicals containing from one to four carbon atoms and includes methyl, ethyl, propyl, isopropyl, t-butyl and the like.

The term "$C_{1-4}$alkoxy" as used herein means straight and branched chain alkoxy radicals containing from one to four carbon atoms and includes methoxy, ethoxy, propyloxy, isopropyloxy, t-butoxy and the like.

The term "cycloalkyloxy" as used herein means saturated carbocylooxy radicals containing from 3–7 carbon atoms and includes cyclopropyloxy, cyclohexyloxy and the like.

The term "1,2-methylenedioxy" as used herein means "—O—CH$_2$—O—" attached to adjacent nodes of a ring.

The term halo as used herein means halogen and includes fluoro, chloro, bromo and the like.

The term "pharmaceutically acceptable salt" means an acid addition salt which is compatible with the treatment of patients.

A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms. The selection criteria for the appropriate salt will be known to one skilled in the art.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol and the like.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "schizophrenia" means schizophrenia, schizophreniform disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington, D.C.

The present invention includes within its scope prodrugs of the compounds of Formula I. In general, such prodrugs will be functional derivatives of the compounds of Formula I which are readily convertible in vivo into the required compound of Formula I. Conventional procedures for the selection and preparation of suitable prodrug derivatives are described, for example, in "Design of Prodrugs" ed. H. Bundgaard, Elsevier, 1985.

In embodiments of the invention, compounds of Formula I include those in which $R^1$ is selected from H and $C_{1-4}$alkyl. Preferably, $R^1$ is methyl. Also within the scope of the invention are compounds of Formula I wherein $R^2$ is selected from H, $C_{1-4}$alkyl and benzyl. In preferred embodiments, $R^2$ is H.

Compounds of the invention include Formula I compounds wherein $R^3$ is selected from $COR^5$ and $SO_2R^5$. Within $R^3$, $R^5$ is selected from phenyl, pyridyl, thienyl, quinolinyl and naphthyl which are optionally substituted with 1–4 substituents selected from $C_{1-4}$alkoxy, $C_{1-4}$alkyl, halo, nitro, trifluoromethyl, trifluoromethoxy, 1,2-methylenedioxy, $C_{1-4}$alkylcarbonyl, $C_{1-4}$alkoxycarbonyl and $C_{1-4}$alkylS—. When $R^3$ is $COR^5$, $R^5$ is specifically selected from phenyl and thienyl optionally substituted with 1–2 groups independently selected from methyl, methoxy, halo and 1,2-methylenedioxy. In preferred embodiments, when $R^3$ is $COR^5$, $R^5$ is phenyl, optionally substituted with 1–2 groups selected independently from halo, methoxy and methyl. When $R^3$ is $SO_2R^5$, $R^5$ is specifically selected from phenyl, naphthyl and thienyl which are all optionally substituted with 1–3 groups independently selected from methyl, methoxy, halo, trifluoromethyl and 1,2-methylenedioxy. In preferred embodiments, when $R^3$ is $SO_2R^5$, $R^5$ is selected from the group consisting of naphthyl and phenyl optionally substituted with 1–3 substituents independently selected from chloro, bromo, fluoro, nitro, methyl and methoxy. In more preferred embodiments, when $R^3$ is $SO_2R^5$, $R^5$ is selected from the group consisting of phenyl, 2-chlorophenyl, 2-bromophenyl, 1-naphthyl, 4-fluorophenyl, 4-chlorophenyl, 4-bromophenyl, 2,4-dichlorophenyl, 3-nitro-4-chlorophenyl, 2,4,6-trimethylphenyl, 4-methyoxyphenyl and 4-methylphenyl.

In further embodiments of the invention, $R^{4b}$ is selected from H, hydroxy, halo, $C_{3-7}$cycloalkyloxy, $C_{1-4}$alkoxy, $C_{1-4}$alkyl, benzyloxy, phenoxy, trifluoromethyl, trifluoromethoxy and vinyl. In specific embodiments, $R^{4b}$ is selected from H, halo, cyclohexyloxy trifluoromethoxy and trifluoromethyl. Preferably, $R^{4b}$ is selected from chloro, trifluoromethoxy, trifluoromethyl and fluoro.

In other embodiments of the invention, $R^{4a}$, $R^{4c}$ and $R^{4d}$ are each independently selected from H, OH, halo, $C_{1-4}$alkyl and $C_{1-4}$alkoxy. In specific embodiments, $R^{4a}$ and $R^{4c}$ are both H and $R^{4d}$ is halo or $R^{4c}$ is halo and $R^{4a}$, $R^{4b}$, $R^{4d}$ are all H. In a preferred embodiment, $R^{4a}$, $R^{4c}$ and $R^{4d}$ are all H.

In another embodiment of the invention, ----- represents a single or double bond. Preferably ----- represents a double bond.

In embodiments of the invention, the compounds of Formula I include:

1-Benzoyl-5-fluoro-3-(1-methyl-1,2,3,6-tetrahydro-4-pyridinyl)indole;

5-Fluoro-1-(4-methylphenylsulfonyl)-3-(1-methyl-1,2,3,6-tetrahydro-4-pyridinyl)indole;

1-(2-Chlorobenzoyl)-5-fluoro-3-(1-methyl-1,2,3,6-tetrahydro-4-pyridinyl)indole;

5-Fluoro-1-(4-methoxybenzoyl)-3-(1-methyl-1,2,3,6-tetrahydro-4-pyridinyl)indole;

5-Fluoro-1-(3,4-methylenedioxybenzoyl)-3-(1-methyl-1,2,3,6-tetrahydro-4-pyridinyl)indole;

1-(2,6-Dichlorobenzoyl)-5-fluoro-3-(1-methyl-1,2,3,6-tetrahydro-4-pyridinyl)indole;

1-Benzoyl-5-bromo-3-(1-methyl-1,2,3,6-tetrahydro-4-pyridinyl)indole;

3-(1-Methyl-1,2,3,6-tetrahydro-4-pyridinyl)-1-phenylsulfonylindole;

1-(4-Methoxyphenylsulfonyl)-3-(1-methyl-1,2,3,6-tetrahydro-4-pyridinyl)indole;

1-(4-Fluorophenylsulfonyl)-3-(1-methyl-1,2,3,6-tetrahydro-4-pyridinyl)indole;

1-(4-Bromophenylsulfonyl)-5-fluoro-3-(1-methyl-1,2,3,6-tetrahydro-4-pyridinyl)indole;

5-Fluoro-1-(2,5-dichlorophenylsulfonyl)-3-(1-methyl-1,2,3,6-tetrahydro-4-pyridinyl)indole;

1-(4-Chloro-3-nitrophenylsulfonyl)-5-fluoro-3-(1-methyl-1,2,3,6-tetrahydro-4-pyridinyl)indole;

5-Fluoro-3-(1-methyl-1,2,3,6-tetrahydro-4-pyridinyl)-1-(2,4,6-trimethylphenylsulfonyl)indole;

5-Fluoro-3-(1-methyl-1,2,3,6-tetrahydro-4-pyridinyl)-1-(2,4,6-triisopropylphenylsulfonyl)indole;

5-Cyclohexyloxy-1-(4-methylphenylsulfonyl)-3-(1-methyl-1,2,3,6-tetrahydro-4-pyridinyl)indole;

6-Bromo-3-(1-methyl-1,2,3,6-tetrahydro-4-pyridinyl)-1-phenylsulfonylindole;

6-Bromo-1-(4-methoxyphenylsulfonyl)-3-(1-methyl-1,2,3,6-tetrahydro-4-pyridinyl)indole;

6-Bromo-1-(4-fluorophenylsulfonyl)-3-(1-methyl-1,2,3,6-tetrahydro-4-pyridinyl)indole;

5-Cyclohexyloxy-3-(1-methyl-1,2,3,6-tetrahydro-4-pyridinyl)-1-phenylsulfonylindole;

5-Cyclohexyloxy-3-(1-methyl-1,2,3,6-tetrahydro-4-pyridinyl)-1-(1-naphthylsulfonyl)indole;

5-Cyclohexyloxy-3-(1-methyl-1,2,3,6-tetrahydro-4-pyridinyl)-1-(2-naphthylsulfonyl)indole;

1-(2-Bromophenylsulfonyl)-5-cyclohexyloxy-3-(1-methyl-1,2,3,6-tetrahydro-4-pyridinyl)indole;

5-Cyclohexyloxy-1-(2,5-dichlorophenylsulfonyl)-3-(1-methyl-1,2,3,6-tetrahydro-4-pyridinyl)indole;

5-Cyclohexyloxy-3-(1-methyl-1,2,3,6-tetrahydro-4-pyridinyl)-1-(2,4,6-trimethylphenylsulfonyl)indole;

5-Cyclohexyloxy-3-(1-methyl-1,2,3,6-tetrahydro-4-pyridinyl)-1-(2,4,6-triisopropylphenylsulfonyl)indole;

5-Cyclohexyloxy-3-(1-methyl-1,2,3,6-tetrahydro-4-pyridinyl)-1-(3-nitrophenylsulfonyl)indole;

1-(4-Chloro-3-nitrophenylsulfonyl)-5-cyclohexyloxy-3-(1-methyl-1,2,3,6-tetrahydro-4-pyridinyl)indole;

5-Cyclohexyloxy-3-(1-methyl-1,2,3,6-tetrahydro-4-pyridinyl)-1-(3-nitro-4-trifluoromethylphenylsulfonyl)indole;

1-(4-Bromophenylsulfonyl)-5-cyclohexyloxy-3-(1-methyl-1,2,3,6-tetrahydro-4-pyridinyl)indole;

5-Cyclohexyloxy-1-(4-methoxyphenylsulfonyl)-3-(1-methyl-1,2,3,6-tetrahydro-4-pyridinyl)indole;

5-Cyclohexyloxy-1-(4-fluorophenylsulfonyl)-3-(1-methyl-1,2,3,6-tetrahydro-4-pyridinyl)indole;

1-(4-Chlorophenylsulfonyl)-5-cyclohexyloxy-3-(1-methyl-1,2,3,6-tetrahydro-4-pyridinyl)indole;

1-(4-t-Butylphenylsulfonyl)-5-cyclohexyloxy-3-(1-methyl-1,2,3,6-tetrahydro-4-pyridinyl)indole;

1-(2-Bromophenylsulfonyl)-5-fluoro-3-(1-methyl-1,2,3,6-tetrahydro-4-pyridinyl)indole;

1-(4-Fluorophenylsulfonyl)-5-fluoro-3-(1-methyl-1,2,3,6-tetrahydro-4-pyridinyl)indole;

1-(4-Chlorophenylsulfonyl)-5-fluoro-3-(1-methyl-1,2,3,6-tetrahydro-4-pyridinyl)indole;

1-(4-$^t$Butylphenylsulfonyl)-4-fluoro-3-(1-methyl-1,2,3,6-tetrahydro-4-pyridinyl)indole;

5-Fluoro-3-(1-methyl-1,2,3,6-tetrahydro-4-pyridinyl)-1-(3-nitrophenylsulfonyl)indole;

5-Fluoro-3-(1-methyl-1,2,3,6-tetrahydro-4-pyridinyl)-1-(1-naphthylsulfonyl)indole;

5-Fluoro-3-(1-methyl-1,2,3,6-tetrahydro-4-pyridinyl)-1-(2-naphthylsulfonyl)indole;

5-Fluoro-3-(1-methyl-1,2,3,6-tetrahydro-4-pyridinyl)-1-phenylsulfonylindole;

5-Chloro-3-(1-methyl-1,2,3,6-tetrahydro-4-pyridinyl)-1-phenylsulfonylindole;

5-Chloro-1-(4-fluorophenylsulfonyl)-3-(1-methyl-1,2,3,6-tetrahydro-4-pyridinyl)indole;

3-(1-Methyl-1,2,3,6-tetrahydro-4-pyridinyl)-1-phenylsulfonyl-5-trifluoromethoxyindole;

1-(4-Fluorophenylsulfonyl)-3-(1-methyl-1,2,3,6-tetrahydro-4-pyridinyl)-5-trifluoromethoxyindole;

1-(4-t-Butylphenylsulfonyl)-3-(1-methyl-1,2,3,6-tetrahydro-4-pyridinyl)-5-trifluoromethoxyindole;

1-(4-Chlorophenylsulfonyl)-3-(1-methyl-1,2,3,6-tetrahydro-4-pyridinyl)-5-trifluoromethoxyindole;

1-(4-Methylphenylsulfonyl)-3-(1-methyl-1,2,3,6-tetrahydro-4-pyridinyl)-5-trifluoromethoxyindole;

(4-Methoxyphenylsulfonyl)-3-(1-methyl-1,2,3,6-tetrahydro-4-pyridinyl)-5-trifluoromethoxyindole;

3-(1-Methyl-1,2,3,6-tetrahydro-4-pyridinyl)-1-phenylsulfonyl-5-trifluoromethylindole hydrochloride;

1-(4-Fluorophenylsulfonyl)-3-(1-methyl-1,2,3,6-tetrahydro-4-pyridinyl)-5-trifluoromethylindole hydrochloride;

1-(4-t-Butylphenylsulfonyl)-3-(1-methyl-1,2,3,6-tetrahydro-4-pyridinyl)-5-trifluoromethylindole hydrochloride;

1-(4-Chlorophenylsulfonyl)-3-(1-methyl-1,2,3,6-tetrahydro-4-pyridinyl)-5-trifluoromethylindole hydrochloride;

1-(4-Methoxyphenylsulfonyl)-3-(1-methyl-1,2,3,6-tetrahydro-4-pyridinyl)-5-trifluoromethylindole hydrochloride;

1-(4-Methylphenylsulfonyl)-3-(1-methyl-1,2,3,6-tetrahydro-4-pyridinyl)-5-trifluoromethylindole hydrochloride;

1-Benzoyl-3-(1-methyl-1,2,3,6-tetrahydro-4-pyridinyl)indole;

1-(4-Methoxybenzoyl)-3-(1-methyl-1,2,3,6-tetrahydro-4-pyridinyl)indole;

1-(4-Fluorobenzoyl)-3-(1-methyl-1,2,3,6-tetrahydro-4-pyridinyl)indole;

1-(2-Chlorobenzoyl)-5-cyclohexyloxy-3-(1-methyl-1,2,3,6-tetrahydro-4-pyridinyl)indole;

5-Cyclohexyloxy-1-(2,6-dichlorobenzoyl)-3-(1-methyl-1,2,3,6-tetrahydro-4-pyridinyl)indole;

5-Cyclohexyloxy-1-(4-methoxybenzoyl)-3-(1-methyl-1,2,3,6-tetrahydro-4-pyridinyl)indole;

5-Cyclohexyloxy-1-(3,4-methyledioxybenzoyl)-3-(1-methyl-1,2,3,6-tetrahydro-4-pyridinyl)indole;

5-Cyclohexyloxy-1-(4-fluorobenzoyl)-3-(1-methyl-1,2,3,6-tetrahydro-4-pyridinyl)indole;

1-Benzoyl-6-bromo-3-(1-methyl-1,2,3,6-tetrahydro-4-pyridinyl)indole;

6-Bromo-1-(4-methoxybenzoyl)-3-(1-methyl-1,2,3,6-tetrahydro-4-pyridinyl)indole;

6-Bromo-1-(4-fluorobenzoyl)-3-(1-methyl-1,2,3,6-tetrahydro-4-pyridinyl)indole;

5-Fluoro-3-(1-methyl-1,2,3,6-tetrahydro-4-pyridinyl)-1-(2-thienoyl)indole;

1-Benzoyl-5-chloro-3-(1-methyl-1,2,3,6-tetrahydro-4-pyridinyl)indole hydrochloride;

1-Benzoyl-3-(1-methyl-1,2,3,6-tetrahydro-4-pyridinyl)-5-trifluoromethoxyindole;

1-(4-Fluorobenzoyl)-3-(1-methyl-1,2,3,6-tetrahydro-4-pyridinyl)-5-trifluoromethoxyindole;

1-(4-Methoxybenzoyl)-3-(1-methyl-1,2,3,6-tetrahydro-4-pyridinyl)-5-trifluoromethoxyindole;

1-(2,6-Dichlorobenzoyl)-3-(1-methyl-1,2,3,6-tetrahydro-4-pyridinyl)-5-trifluoromethoxyindole;

1-Benzoyl-3-(1-methyl-1,2,3,6-tetrahydro-4-pyridinyl)-5-trifluoromethylindole hydrochloride;

1-(4-Fluorobenzoyl)-3-(1-methyl-1,2,3,6-tetrahydro-4-pyridinyl)-5-trifluoromethylindole;

1-(2,6-Dichlorobenzoyl)-3-(1-methyl-1,2,3,6-tetrahydro-4-pyridinyl)-5-trifluoromethylindole;

5-Cyclohexyloxy-1-(4-methylphenylsulfonyl)-3-(1-methyl-4-piperidinyl)indole;

5-Chloro-3-(1-methyl-4-piperidinyl)-1-phenylsulfonylindole;

5-Chloro-1-(4-fluorophenylsulfonyl)-3-(1-methyl-4-piperidinyl)indole;

3-(1-Methyl-4-piperidinyl)-1-phenylsulfonylindole;

1-(4-Fluorophenylsulfonyl)-3-(1-methyl-4-piperidinyl)indole;

6-Chloro-3-(1-methyl-4-piperidinyl)-1-phenylsulfonylindole;

1-(4-Fluorophenylsulfonyl)-6-chloro-3-(1-methyl-4-piperidinyl)indole;

5-Fluoro-1-phenylsulfonyl-3-(1-methyl-4-piperidinyl)indole;

1-(4-Fluorophenylsulfonyl)-5-fluoro-3-(1-methyl-4-piperidinyl)indole;

1-Benzoyl-5-chloro-3-(1-methyl-4-piperidinyl)indole;

5-Chloro-1-(4-fluorobenzoyl)-3-(1-methyl-4-piperidinyl)indole;

1-Benzoyl-3-(1-methyl-4-piperidinyl)indole;

1-(4-Fluorobenzoyl)-3-(1-methyl-4-piperidinyl)indole;

1-Benzoyl-6-chloro-3-(1-methyl-4-piperidinyl)indole;

6-Chloro-1-(4-fluorobenzoyl)-3-(1-methyl-4-piperidinyl)indole;

1-Benzoyl-5-fluoro-3-(1-methyl-4-piperidinyl)indole;

1-(4-Fluorobenzoyl)-5-fluoro-3-(1-methyl-4-piperidinyl)indole;

1-Benzoyl-3-(1-methyl-1,2,3,6-tetrahydro-4-pyridinyl)-5-vinylindole;

5,7-Difluoro-3-(1-methyl-1,2,3,6-tetrahydro-4-pyridinyl)-1-phenylsulfonylindole;

5,7-Difluoro-3-(1-methyl-1,2,3,6-tetrahydro-4-pyridinyl)-1-(4-methylphenylsulfonyl)indole;

5,7-Difluoro-1-(4-fluorophenylsulfonyl)-3-(1-methyl-1,2,3,6-tetrahydro-4-pyridinyl)indole;

1-(4-Bromophenylsulfonyl)-5,7-difluoro-3-(1-methyl-1,2,3,6-tetrahydro-4-pyridinyl)indole;

1-(4-Chlorophenylsulfonyl)-5,7-difluoro-3-(1-methyl-1,2,3,6-tetrahydro-4-pyridinyl)indole;

5,7-Difluoro-3-(1-methyl-1,2,3,6-tetrahydro-4-pyridinyl)-1-(1-naphthylsulfonyl)indole;

5,7-Difluoro-3-(1-methyl-1,2,3,6-tetrahydro-4-pyridinyl)-1-(2-naphthylsulfonyl)indole;

5,7-Difluoro-3-(1-methyl-1,2,3,6-tetrahydro-4-pyridinyl)-1-(2,4,6-trimethylphenyl)sulfonylindole;

5,7-Difluoro-1-(4-fluorobenzoyl)-3-(1-methyl-1,2,3,6-tetrahydro-4-pyridinyl)indole; and 1-(2,5-Dichlorobenzoyl)-5,7-difluoro-3-(1-methyl-1,2,3,6-tetrahydro-4-pyridinyl)indole.

In specific embodiments of the invention, the compounds of Formula I include:

1-Benzoyl-5-fluoro-3-(1-methyl-1,2,3,6-tetrahydro-4-pyridinyl)indole;

5-Fluoro-1-(4-methylphenylsulfonyl)-3-(1-methyl-1,2,3,6-tetrahydro-4-pyridinyl)indole;

1-(2-Chlorobenzoyl)-5-fluoro-3-(1-methyl-1,2,3,6-tetrahydro-4-pyridinyl)indole;

1-(2,6-Dichlorobenzoyl)-5-fluoro-3-(1-methyl-1,2,3,6-tetrahydro-4-pyridinyl)indole;

1-Benzoyl-5-bromo-3-(1-methyl-1,2,3,6-tetrahydro-4-pyridinyl)indole;

3-(1-Methyl-1,2,3,6-tetrahydro-4-pyridinyl)-1-phenylsulfonylindole;

1-(4-Methoxyphenylsulfonyl)-3-(1-methyl-1,2,3,6-tetrahydro-4-pyridinyl)indole;

1-(4-Fluorophenylsulfonyl)-3-(1-methyl-1,2,3,6-tetrahydro-4-pyridinyl)indole;

1-(4-Bromophenylsulfonyl)-5-fluoro-3-(1-methyl-1,2,3,6-tetrahydro-4-pyridinyl)indole;

5-Fluoro-1-(2,5-dichlorophenylsulfonyl)-3-(1-methyl-1,2,3,6-tetrahydro-4-pyridinyl)indole;

1-(4-Chloro-3-nitrophenylsulfonyl)-5-fluoro-3-(1-methyl-1,2,3,6-tetrahydro-4-pyridinyl)indole;

5-Fluoro-3-(1-methyl-1,2,3,6-tetrahydro-4-pyridinyl)-1-(2,4,6-trimethylphenylsulfonyl)indole;

5-Cyclohexyloxy-1-(4-methylphenylsulfonyl)-3-(1-methyl-1,2,3,6-tetrahydro-4-pyridinyl)indole;

6-Bromo-3-(1-methyl-1,2,3,6-tetrahydro-4-pyridinyl)-1-phenylsulfonylindole;

6-Bromo-1-(4-methoxyphenylsulfonyl)-3-(1-methyl-1,2,3,6-tetrahydro-4-pyridinyl)indole;

6-Bromo-1-(4-fluorophenylsulfonyl)-3-(1-methyl-1,2,3,6-tetrahydro-4-pyridinyl)indole;

5-Cyclohexyloxy-3-(1-methyl-1,2,3,6-tetrahydro-4-pyridinyl)-1-phenylsulfonylindole;

5-Cyclohexyloxy-3-(1-methyl-1,2,3,6-tetrahydro-4-pyridinyl)-1-(1-naphthylsulfonyl)indole;

5-Cyclohexyloxy-3-(1-methyl-1,2,3,6-tetrahydro-4-pyridinyl)-1-(2-naphthylsulfonyl)indole;

1-(2-Bromophenylsulfonyl)-5-cyclohexyloxy-3-(1-methyl-1,2,3,6-tetrahydro-4-pyridinyl)indole;

5-Cyclohexyloxy-3-(1-methyl-1,2,3,6-tetrahydro-4-pyridinyl)-1-(3-nitrophenylsulfonyl)indole;

5-Cyclohexyloxy-3-(1-methyl-1,2,3,6-tetrahydro-4-pyridinyl)-1-(3-nitro-4-trifluoromethylphenylsulfonyl)indole;

1-(4-Bromophenylsulfonyl)-5-cyclohexyloxy-3-(1-methyl-1,2,3,6-tetrahydro-4-pyridinyl)indole;

5-Cyclohexyloxy-1-(4-methoxyphenylsulfonyl)-3-(1-methyl-1,2,3,6-tetrahydro-4-pyridinyl)indole;

5-Cyclohexyloxy-1-(4-fluorophenylsulfonyl)-3-(1-methyl-1,2,3,6-tetrahydro-4-pyridinyl)indole;

1-(4-Chlorophenylsulfonyl)-5-cyclohexyloxy-3-(1-methyl-1,2,3,6-tetrahydro-4-pyridinyl)indole;

1-(4-t-Butylphenylsulfonyl)-5-cyclohexyloxy-3-(1-methyl-1,2,3,6-tetrahydro-4-pyridinyl)indole;

1-(2-Bromophenylsulfonyl)-5-fluoro-3-(1-methyl-1,2,3,6-tetrahydro-4-pyridinyl)indole;

1-(4-Fluorophenylsulfonyl)-5-fluoro-3-(1-methyl-1,2,3,6-tetrahydro-4-pyridinyl)indole;

1-(4-Chlorophenylsulfonyl)-5-fluoro-3-(1-methyl-1,2,3,6-tetrahydro-4-pyridinyl)indole;

1-(4-t-Butylphenylsulfonyl)-4-fluoro-3-(1-methyl-1,2,3,6-tetrahydro-4-pyridinyl)indole;

5-Fluoro-3-(1-methyl-1,2,3,6-tetrahydro-4-pyridinyl)-1-(3-nitrophenylsulfonyl)indole;

5-Fluoro-3-(1-methyl-1,2,3,6-tetrahydro-4-pyridinyl)-1-(1-naphthylsulfonyl)indole;

5-Fluoro-3-(1-methyl-1,2,3,6-tetrahydro-4-pyridinyl)-1-(2-naphthylsulfonyl)indole;

5-Fluoro-3-(1-methyl-1,2,3,6-tetrahydro-4-pyridinyl)-1-phenylsulfonylindole;

5-Chloro-3-(1-methyl-1,2,3,6-tetrahydro-4-pyridinyl)-1-phenylsulfonylindole;

5-Chloro-1-(4-fluorophenylsulfonyl)-3-(1-methyl-1,2,3,6-tetrahydro-4-pyridinyl)indole;

3-(1-Methyl-1,2,3,6-tetrahydro-4-pyridinyl)-1-phenylsulfonyl-5-trifluoromethoxyindole;

1-(4-Fluorophenylsulfonyl)-3-(1-methyl-1,2,3,6-tetrahydro-4-pyridinyl)-5-trifluoromethoxyindole;

1-(4-t-Butylphenylsulfonyl)-3-(1-methyl-1,2,3,6-tetrahydro-4-pyridinyl)-5-trifluoromethoxyindole;

1-(4-Chlorophenylsulfonyl)-3-(1-methyl-1,2,3,6-tetrahydro-4-pyridinyl)-5-trifluoromethoxyindole;

1-(4-Methylphenylsulfonyl)-3-(1-methyl-1,2,3,6-tetrahydro-4-pyridinyl)-5-trifluoromethoxyindole;

(4-Methoxyphenylsulfonyl)-3-(1-methyl-1,2,3,6-tetrahydro-4-pyridinyl)-5-trifluoromethoxyindole;

3-(1-Methyl-1,2,3,6-tetrahydro-4-pyridinyl)-1-phenylsulfonyl-5-trifluoromethylindole hydrochloride;

1-(4-Fluorophenylsulfonyl)-3-(1-methyl-1,2,3,6-tetrahydro-4-pyridinyl)-5-trifluoromethylindole hydrochloride;

1-(4-t-Butylphenylsulfonyl)-3-(1-methyl-1,2,3,6-tetrahydro-4-pyridinyl)-5-trifluoromethylindole hydrochloride;

1-(4-Chlorophenylsulfonyl)-3-(1-methyl-1,2,3,6-tetrahydro-4-pyridinyl)-5-trifluoromethylindole hydrochloride;

1-(4-Methoxyphenylsulfonyl)-3-(1-methyl-1,2,3,6-tetrahydro-4-pyridinyl)-5-trifluoromethylindole hydrochloride;

1-(4-Methylphenylsulfonyl)-3-(1-methyl-1,2,3,6-tetrahydro-4-pyridinyl )-5-trifluoromethylindole hydrochloride;

1-(2-Chlorobenzoyl)-5-cyclohexyloxy-3-(1-methyl-1,2,3,6-tetrahydro-4-pyridinyl)indole;
5-Cyclohexyloxy-1-(2,6-dichlorobenzoyl)-3-(1-methyl-1,2,3,6-tetrahydro-4-pyridinyl)indole;
5-Cyclohexyloxy-1-(3,4-methylediooxybenzoyl)-3-(1-methyl-1,2,3,6-tetrahydro-4-pyridinyl)indole;
5-Cyclohexyloxy-1-(4-fluorobenzoyl)-3-(1-methyl-1,2,3,6-tetrahydro-4-pyridinyl)indole;
1-Benzoyl-5-chloro-3-(1-methyl-1,2,3,6-tetrahydro-4-pyridinyl)indole hydrochloride;
1-Benzoyl-3-(1-methyl-1,2,3,6-tetrahydro-4-pyridinyl)-5-trifluoromethoxyindole;
1-(4-Fluorobenzoyl)-3-(1-methyl-1,2,3,6-tetrahydro-4-pyridinyl)-5-trifluoromethoxyindole;
1-(2,6-Dichlorobenzoyl)-3-(1-methyl-1,2,3,6-tetrahydro-4-pyridinyl)-5-trifluoromethoxyindole;
1-Benzoyl-3-(1-methyl-1,2,3,6-tetrahydro-4-pyridinyl)-5-trifluoromethylindole hydrochloride;
1-(4-Fluorobenzoyl)-3-(1-methyl-1,2,3,6-tetrahydro-4-pyridinyl)-5-trifluoromethylindole;
1-(2,6-Dichlorobenzoyl)-3-(1-methyl-1,2,3,6-tetrahydro-4-pyridinyl)-5-trifluoromethylindole;
5-Chloro-3-(1-methyl-4-piperidinyl)-1-phenylsulfonylindole;
5-Chloro-1-(4-fluorophenylsulfonyl)-3-(1-methyl-4-piperidinyl)indole;
3-(1-Methyl-4-piperidinyl)-1-phenylsulfonylindole;
1-(4-Fluorophenylsulfonyl)-3-(1-methyl-4-piperidinyl)indole;
1-(4-Fluorophenylsulfonyl)-6-chloro-3-(1-methyl-4-piperidinyl)indole;
5-Fluoro-1-phenylsulfonyl-3-(1-methyl-4-piperidinyl)indole;
5,7-Difluoro-3-(1-methyl-1,2,3,6-tetrahydro-4-pyridinyl)-1-phenylsulfonylindole;
5,7-Difluoro-3-(1-methyl-1,2,3,6-tetrahydro-4-pyridinyl)-1-(4-methylphenylsulfonyl)indole;
5,7-Difluoro-1-(4-fluorophenylsulfonyl)-3-(1-methyl-1,2,3,6-tetrahydro-4-pyridinyl)indole;
1-(4-Bromophenylsulfonyl)-5,7-difluoro-3-(1-methyl-1,2,3,6-tetrahydro-4-pyridinyl)indole;
1-(4-Chlorophenylsulfonyl)-5,7-difluoro-3-(1-methyl-1,2,3,6-tetrahydro-4-pyridinyl)indole;
5,7-Difluoro-3-(1-methyl-1,2,3,6-tetrahydro-4-pyridinyl)-1-(1-naphthylsulfonyl)indole;
5,7-Difluoro-3-(1-methyl-1,2,3,6-tetrahydro-4-pyridinyl)-1-(2-naphthylsulfonyl)indole;
5,7-Difluoro-3-(1-methyl-1,2,3,6-tetrahydro-4-pyridinyl)-1-(2,4,6-trimethylphenyl)sulfonylindole;
5,7-Difluoro-1-(4-fluorobenzoyl)-3-(1-methyl-1,2,3,6-tetrahydro-4-pyridinyl)indole; and
1-(2,5-Dichlorobenzoyl)-5,7-difluoro-3-(1-methyl-1,2,3,6-tetrahydro-4-pyridinyl)indole.

In more specific embodiments of the invention, the compounds of Formula I include:

5-Fluoro-1-(4-methylphenylsulfonyl)-3-(1-methyl-1,2,3,6-tetrahydro-4-pyridinyl)indole;
1-(2-Chlorobenzoyl)-5-fluoro-3-(1-methyl-1,2,3,6-tetrahydro-4-pyridinyl)indole;
1-(2,6-Dichlorobenzoyl)-5-fluoro-3-(1-methyl-1,2,3,6-tetrahydro-4-pyridinyl)indole;
1-Benzoyl-5-bromo-3-(1-methyl-1,2,3,6-tetrahydro-4-pyridinyl)indole;
3-(1-Methyl-1,2,3,6-tetrahydro-4-pyridinyl)-1-phenylsulfonylindole;
1-(4-Methoxyphenylsulfonyl)-3-(1-methyl-1,2,3,6-tetrahydro-4-pyridinyl)indole;
1-(4-Fluorophenylsulfonyl)-3-(1-methyl-1,2,3,6-tetrahydro-4-pyridinyl)indole;
1-(4-Bromophenylsulfonyl)-5-fluoro-3-(1-methyl-1,2,3,6-tetrahydro-4-pyridinyl)indole;
5-Fluoro-1-(2,5-dichlorophenylsulfonyl)-3-(1-methyl-1,2,3,6-tetrahydro-4-pyridinyl)indole;
1-(4-Chloro-3-nitrophenylsulfonyl)-5-fluoro-3-(1-methyl-1,2,3,6-tetrahydro-4-pyridinyl)indole;
5-Fluoro-3-(1-methyl-1,2,3,6-tetrahydro-4-pyridinyl)-1-(2,4,6-trimethylphenylsulfonyl)indole;
5-Cyclohexyloxy-1-(4-methylphenylsulfonyl)-3-(1-methyl-1,2,3,6-tetrahydro-4-pyridinyl)indole;
6-Bromo-3-(1-methyl-1,2,3,6-tetrahydro-4-pyridinyl)-1-phenylsulfonylindole;
6-Bromo-1-(4-fluorophenylsulfonyl)-3-(1-methyl-1,2,3,6-tetrahydro-4-pyridinyl)indole;
5-Cyclohexyloxy-3-(1-methyl-1,2,3,6-tetrahydro-4-pyridinyl)-1-phenylsulfonylindole;
5-Cyclohexyloxy-3-(1-methyl-1,2,3,6-tetrahydro-4-pyridinyl)-1-(1-naphthylsulfonyl)indole;
5-Cyclohexyloxy-3-(1-methyl-1,2,3,6-tetrahydro-4-pyridinyl)-1-(2-naphthylsulfonyl)indole;
1-(2-Bromophenylsulfonyl)-5-cyclohexyloxy-3-(1-methyl-1,2,3,6-tetrahydro-4-pyridinyl)indole;
5-Cyclohexyloxy-1-(4-methoxyphenylsulfonyl)-3-(1-methyl-1,2,3,6-tetrahydro-4-pyridinyl)indole;
1-(2-Bromophenylsulfonyl)-5-fluoro-3-(1-methyl-1,2,3,6-tetrahydro-4-pyridinyl)indole;
1-(4-Fluorophenylsulfonyl)-5-fluoro-3-(1-methyl-1,2,3,6-tetrahydro-4-pyridinyl)indole;
1-(4-Chlorophenylsulfonyl)-5-fluoro-3-(1-methyl-1,2,3,6-tetrahydro-4-pyridinyl)indole;
5-Fluoro-3-(1-methyl-1,2,3,6-tetrahydro-4-pyridinyl)-1-(3-nitrophenylsulfonyl)indole;
5-Fluoro-3-(1-methyl-1,2,3,6-tetrahydro-4-pyridinyl)-1-(1-naphthylsulfonyl)indole;
5-Fluoro-3-(1-methyl-1,2,3,6-tetrahydro-4-pyridinyl)-1-(2-naphthylsulfonyl)indole;
5-Fluoro-3-(1-methyl-1,2,3,6-tetrahydro-4-pyridinyl)-1-phenylsulfonylindole;
5-Chloro-3-(1-methyl-1,2,3,6-tetrahydro-4-pyridinyl)-1-phenylsulfonylindole;
5-Chloro-1-(4-fluorophenylsulfonyl)-3-(1-methyl-1,2,3,6-tetrahydro-4-pyridinyl)indole;
1-(4-Chlorophenylsulfonyl)-3-(1-methyl-1,2,3,6-tetrahydro-4-pyridinyl)-5-trifluoromethoxyindole;
1-(4-Methylphenylsulfonyl)-3-(1-methyl-1,2,3,6-tetrahydro-4-pyridinyl)-5-trifluoromethoxyindole;
3-(1-Methyl-1,2,3,6-tetrahydro-4-pyridinyl)-1-phenylsulfonyl-5-trifluoromethylindole hydrochloride;
1-(4-Chlorophenylsulfonyl)-3-(1-methyl-1,2,3,6-tetrahydro-4-pyridinyl)-5-trifluoromethylindole hydrochloride;
1-(4-Methoxyphenylsulfonyl)-3-(1-methyl-1,2,3,6-tetrahydro-4-pyridinyl)-5-trifluoromethylindole hydrochloride;
1-(4-Methylphenylsulfonyl)-3-(1-methyl-1,2,3,6-tetrahydro-4-pyridinyl)-5-trifluoromethylindole hydrochloride;

1-(2-Chlorobenzoyl)-5-cyclohexyloxy-3-(1-methyl-1,2,
3,6-tetrahydro-4-pyridinyl)indole;

1-Benzoyl-5-chloro-3-(1-methyl-1,2,3,6-tetrahydro-4-
pyridinyl)indole hydrochloride;

1-(2,6-Dichlorobenzoyl)-3-(1-methyl-1,2,3,6-tetrahydro-
4-pyridinyl)-5-trifluoromethylindole;

3-(1-Methyl-4-piperidinyl)-1-phenylsulfonylindole;

5,7-Difluoro-3-(1-methyl-1,2,3,6-tetrahydro-4-
pyridinyl)-1-phenylsulfonylindole;

5,7-Difluoro-3-(1-methyl-1,2,3,6-tetrahydro-4-
pyridinyl)-1-(4-methylphenylsulfonyl)indole;

1-(4-Bromophenylsulfonyl)-5,7-difluoro-3-(1-methyl-1,
2,3,6-tetrahydro-4-pyridinyl)indole;

1-(4-Chlorophenylsulfonyl)-5,7-difluoro-3-(1-methyl-1,
2,3,6-tetrahydro-4-pyridinyl)indole;

5,7-Difluoro-3-(1-methyl-1,2,3,6-tetrahydro-4-
pyridinyl)-1-(1-naphthylsulfonyl)indole;

5,7-Difluoro-3-(1-methyl-1,2,3,6-tetrahydro-4-
pyridinyl)-1-(2-naphthylsulfonyl)indole;

5,7-Difluoro-1-(4-fluorobenzoyl)-3-(1-methyl-1,2,3,6-
tetrahydro-4-pyridinyl)indole; and 1-(2,5-Dichlorobenzoyl)-5,7-difluoro-3-(1-methyl-1,2,3,
6-tetrahydro-4-pyridinyl)indole.

In the most specific embodiments of the invention, the compounds of Formula I include:

5-Fluoro-1-(4-methylphenylsulfonyl)-3-(1-methyl-1,2,3,
6-tetrahydro-4-pyridinyl)indole;

1-(2-Chlorobenzoyl)-5-fluoro-3-(1-methyl-1,2,3,6-
tetrahydro-4-pyridinyl)indole;

1-(2,6-Dichlorobenzoyl)-5-fluoro-3-(1-methyl-1,2,3,6-
tetrahydro-4-pyridinyl)indole;

3-(1-Methyl-1,2,3,6-tetrahydro-4-pyridinyl)-1-
phenylsulfonylindole;

1-(4-Fluorophenylsulfonyl)-3-(1-methyl-1,2,3,6-
tetrahydro-4-pyridinyl)indole;

1-(2-Bromophenylsulfonyl)-5-fluoro-3-(1-methyl-1,2,3,
6-tetrahydro-4-pyridinyl)indole;

1-(4-Fluorophenylsulfonyl)-5-fluoro-3-(1-methyl-1,2,3,
6-tetrahydro-4-pyridinyl)indole;

1-(4-Chlorophenylsulfonyl)-5-fluoro-3-(1-methyl-1,2,3,
6-tetrahydro-4-pyridinyl)indole;

5-Fluoro-3-(1-methyl-1,2,3,6-tetrahydro-4-pyridinyl)-1-
(1-naphthylsulfonyl)indole;

5-Fluoro-3-(1-methyl-1,2,3,6-tetrahydro-4-pyridinyl)-1-
phenylsulfonylindole;

5-Chloro-3-(1-methyl-1,2,3,6-tetrahydro-4-pyridinyl)-1-
phenylsulfonylindole;

5-Chloro-1-(4-fluorophenylsulfonyl)-3-(1-methyl-1,2,3,
6-tetrahydro-4-pyridinyl)indole;

1-(4-Chlorophenylsulfonyl)-3-(1-methyl-1,2,3,6-
tetrahydro-4-pyridinyl)-5-trifluoromethoxyindole;

1-(4-Methylphenylsulfonyl)-3-(1-methyl-1,2,3,6-
tetrahydro-4-pyridinyl)-5-trifluoromethoxyindole;

3-(1-Methyl-1,2,3,6-tetrahydro-4-pyridinyl)-1-
phenylsulfonyl-5-trifluoromethylindole hydrochloride;

1-(2-Chlorobenzoyl)-5-cyclohexyloxy-3-(1-methyl-1,2,
3,6-tetrahydro-4-pyridinyl)indole;

5,7-Difluoro-3-(1-methyl-1,2,3,6-tetrahydro-4-
pyridinyl)-1-phenylsulfonylindole;

5,7-Difluoro-3-(1-methyl-1,2,3,6-tetrahydro-4-
pyridinyl)-1-(4-methylphenylsulfonyl)indole 1-(4-Bromophenylsulfonyl)-5,7-difluoro-3-(1-methyl-1,
2,3,6-tetrahydro-4-pyridinyl)indole;

1-(4-Chlorophenylsulfonyl)-5,7-difluoro-3-(1-methyl-1,
2,3,6-tetrahydro-4-pyridinyl)indole;

5,7-Difluoro-3-(1-methyl-1,2,3,6-tetrahydro-4-
pyridinyl)-1-(1-naphthylsulfonyl)indole;

5,7-Difluoro-3-(1-methyl-1,2,3,6-tetrahydro-4-
pyridinyl)-1-(2-naphthylsulfonyl)indole; and 5,7-Difluoro-1-(4-fluorobenzoyl)-3-(1-methyl-1,2,3,6-
tetrahydro-4-pyridinyl)indole.

Acid addition salts of the compounds of Formula I are most suitably formed from pharmaceutically acceptable acids, and include for example those formed with inorganic acids e.g. hydrochloric, sulfuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

Compounds of the present invention may have within its structure a chiral centre. The invention extends to cover all structural and optical isomers of the various compounds, as well as racemic mixtures thereof.

In accordance with other aspects of the invention, the compounds of the present invention can be prepared by processes analogous to those established in the art. For example, as shown in Scheme 1, compounds of Formula I may be prepared by first treating compounds of Formula A, wherein $R^1$ is $C_{1-4}$alkyl and $R^2$ and $R^{4a-d}$ are as defined in Formula I, with an appropriate base, followed by the addition of a reagent of either Formula B or C, which provides a compound of Formula I wherein $R^3$ is $SO_2R^5$ or $COR^5$, respectively. Therefore, for example, treatment of compounds of Formula A with a strong base such as lithium diisopropylamide, n-butyllithium or sodium bis (trimethylsilyl)amide in an inert solvent such as tetrahydrofuran or hexanes at a temperature in the range of −100 to 0° C. or, alternatively an organic amine in the presence of 4-dimethylaminopyridine (DMAP), in an inert solvent such as methylene chloride or chloroform, at a temperature in the range of 0–60° C., followed by the addition of acid chlorides of Formula B or sulfonyl chlorides of Formula C, wherein $R^5$ is as defined in Formula I, provides compounds of Formula I wherein $R^3$ is $COR^5$ or $SO_2R^5$ respectively. Preferred conditions are sodium bis(trimethylsilyl)amide in tetrahydrofuran at −78° C. followed by warming to room temperature or triethylamine and DMAP in methylene chloride at room temperature. Reagents B and C are commercially available or can be prepared using standard methods known to those skilled in the art. The preparation of compounds of Formula A is described below.

Scheme 1

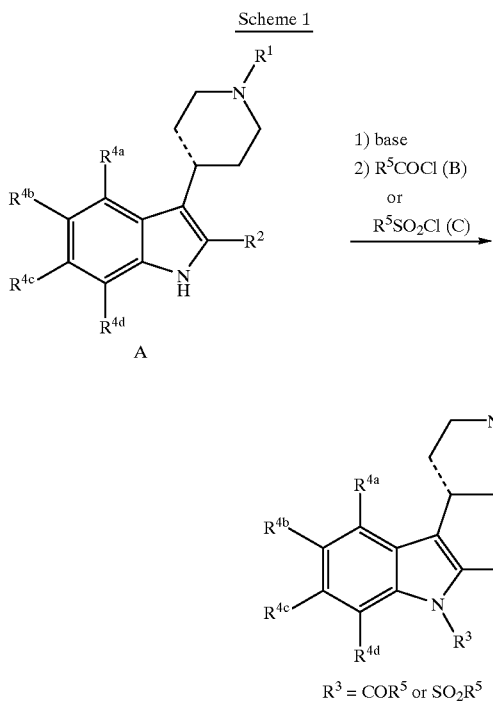

R³ = COR⁵ or SO₂R⁵

Compounds of Formula I wherein $R^1$ is H may be prepared by treating a compound of Formula A, wherein $R^1$ is a suitable protecting group such as t-butoxycarbonyl (t-BOC), with reagents of Formula A or B as described above. Removal of the protecting group may be performed under standard conditions, for example using acidic conditions such as HCl in ethyl acetate to remove the t-BOC group, to provide compounds of Formula I wherein $R^1$ is H.

Compounds of Formula I, wherein $R^2$ is selected from $C_{1-4}$alkyl and benzyl, $R^1$ is $C_{1-4}$alkyl, $R^3$ is $SO_2R^5$ and $R^{4a-d}$ are as defined in Formula I, may also be prepared by treating compounds of Formula I, wherein $R^2$ is H, $R^1$ is selected from $C_{1-4}$alkyl, $R^3$ is $SO_2R^5$ and $R^{4a-d}$ are as defined in Formula I, with a strong base, such as n-butyllithium, in an inert solvent, such as tetrahydrofuran, at a temperature in the range of –100–0° C. (preferably -78° C.), followed by the addition of a reagent of formula $R^2$-X, wherein $R^2$ is selected from $C_{1-4}$alkyl and benzyl and X is a suitable leaving group such as bromo, followed by warming to room temperature. The above reaction may also be carried out on a compound of Formula I, wherein $R^2$ is H, $R^1$ is a suitable protecting group, such as t-butoxycarbonyl, $R^3$ is $SO_2R^5$ and $R^{4a-d}$ are as defined in Formula I, which, after removal of the protecting group using standard deprotection conditions (for example HCl in ethyl acetate to remove the t-butoxycarbonyl protecting group), provides a compound of Formula I wherein $R^2$ is selected from $C_{1-4}$alkyl and benzyl, $R^1$ is H, $R^3$ is $SO_2R^5$ and $R^{4a-c}$ are as defined in Formula I.

Compounds of Formula A wherein $R^1$, $R^2$ and $R^{4a-d}$ are as defined in Formula I may be prepared as shown in Scheme 2. Indole D, wherein $R^2$ and $R^{4a-d}$ are as defined in Formula I, may be condensed with a reagent of Formula E, wherein $R^1$ is as defined in Formula I, in the presence of a base in a suitable solvent at temperatures in the range of 25–100° C., preferably, 60–90° C. to provide compounds of Formula A wherein $R^1$, $R^2$, $R^{4a-d}$ are as defined in Formula I and ----- represents a double bond. Suitable bases include organic amines such as pyrrolidine or triethylamine and suitable solvents include methanol, ethanol and the like. Preferred conditions are pyrrolidine in ethanol at a refluxing temperature. Compounds of Formula A, wherein $R^1$, $R^2$, $R^{4a-d}$ are as defined in Formula I and ----- represents a double bond, may be reduced using standard hydrogenation conditions or using metal hydride reducing reagents to provide compounds of Formula A where $R^1$, $R^2$, $R^{4a-d}$ are as defined in Formula I and ----- represents a single bond as shown in Scheme 2. Preferred is reduction by hydrogenation, using a suitable catalyst such as palladium or platinum on carbon in methanol at room temperature.

Scheme 2

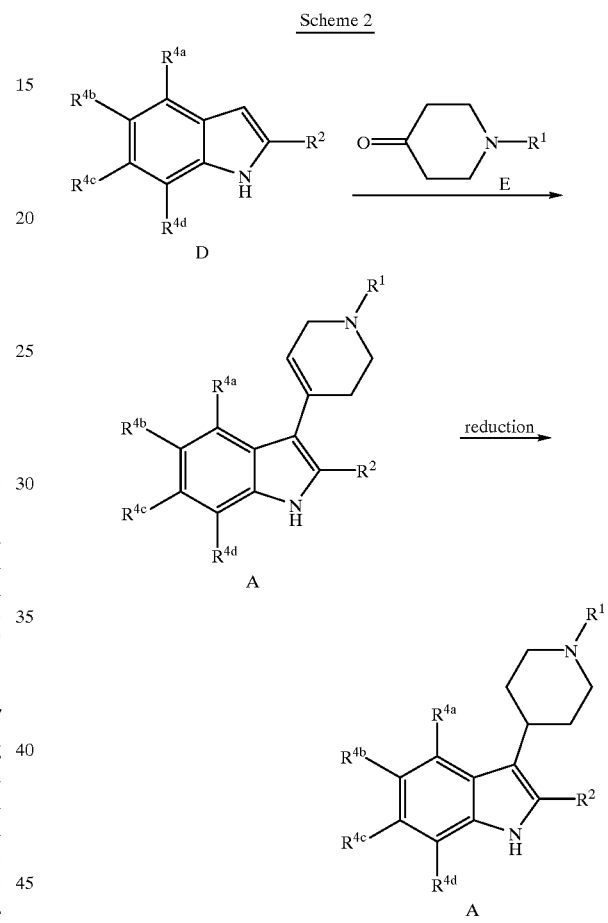

Reagents of Formula A, wherein $R^1$ is a protecting group and $R^2$ and $R^{4a-d}$ are as defined in Formula I, are available by treating reagents of Formula A, wherein $R^1$ is H, $R^2$ and $R^{4a-d}$ are as defined in Formula I and ----- represents a single or double bond, under standard conditions to introduce a protecting group on the piperidine or tetrahydropyridine nitrogen. For example, reaction of indole A, wherein $R^1$ is H, in the presence of di-t-butyldicarbonate and a base, such as sodium hydroxide, would provide compounds of Formula A wherein $R^1$ is the t-BOC protecting group, $R^2$ and $R^{4a-d}$ are as defined in Formula I and ----- represents a single or double bond.

The indoles of Formula D are either commercially available or can be prepared using standard procedures. For example, compounds of Formula D may be prepared as shown in Scheme 3. 4-Substituted anilines of Formula E, wherein $R^{4a-d}$ are as defined in Formula I, can be treated with reagents of Formula F, wherein R is as defined in Formula I, in the presence of a base such as sodium bicarbonate or potassium carbonate in an alcoholic solvent at temperatures in the range of 60–100 °C., to provide intermediates of Formula G. Preferred conditions are sodium bicarbonate in ethanol at around 80° C. Intermediates of Formula G can be cyclized in the presence of reagents of Formula H, wherein R is, for example, methyl or trifluoromethyl (which is preferred) at temperatures in the range of 60–100° C., to provide indoles of Formula J. The preferred conditions are trifluoroacetic anhydride and trifluoroacetic acid at refluxing temperatures. Finally, compounds of Formula J can be treated under standard deprotection conditions, for example alkali hydroxides in an alcoholic solvent, to provide indoles of Formula D, wherein $R^2$ and $R^{4a-d}$ are as defined in Formula I. Preferred conditions for this reaction are potassium hydroxide in ethanol at room temperature. The reagents of Formula E and F, are either commercially available or can be prepared using processes analogous to those established in the art.

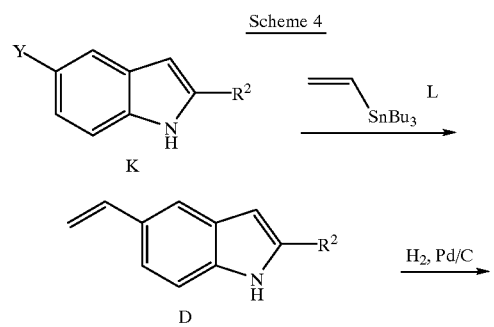

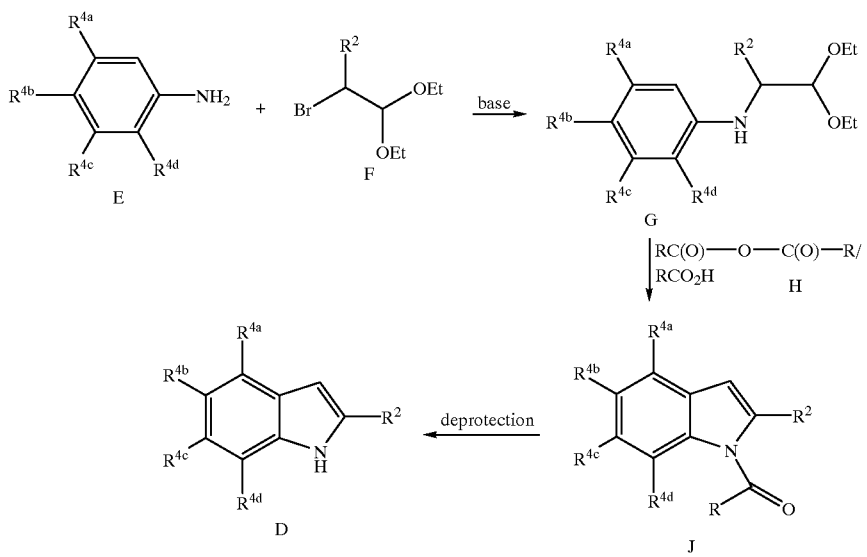

An alternative procedure for preparing indoles of Formula D wherein $R^{4b}$ is vinyl or ethyl is shown in Scheme 4. Indoles of Formula K, wherein Y is a suitable leaving group such as halo or triflate (preferably bromo) and $R^2$ is as defined in Formula I, can be coupled with a vinyl trialkylstannane of, for example, Formula L, under standard palladium-cross coupling conditions to provide indoles of Formula D, wherein $R^{4b}$ is vinyl and $R^2$ is as defined in Formula I. It will be appreciated that other metal coupling reagents could be used in place of the vinyl stannane, for example, a vinyl boronic acid, chloro zinc and the like. Preferred coupling conditions include heating the indole and vinyl metal reagent in an inert solvent such as dimethylformamide or toluene in the presence of tetrakis (triphenylphosphine) palladium (0) at refluxing temperatures. Following the coupling reaction, the double bond of the vinyl group can be hydrogenated using catalytic amounts of palladium on carbon in an inert solvent (preferably ethyl acetate) in a hydrogen atmosphere at room temperature to provide indoles of Formula D wherein $R^{4b}$ is ethyl. This procedure could also be used to prepare compounds of Formula D wherein $R^{4a}$, $R^{4c}$ or $R^{4d}$ are ethyl by reacting the appropriately substituted indole L as described above.

-continued

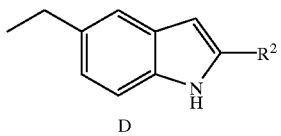

Indoles of Formula D, wherein $R^{4b}$ is cyclooxy or phenoxy and $R^2$ is as defined in Formula I, are also available from the corresponding 5-hydroxyindole M as shown in Scheme 5. Reaction of indole M with, for example, cyclohexanol N under standard Mitsunobu conditions (Mitsunobu, O. *Synthesis*, 1981:1–28) provides reagents of Formula D, wherein $R^{4b}$ is cyclohexyloxy and $R^2$ is as defined as Formula I. Reaction of indole M with reagent of Formula O wherein Y is an appropriate leaving group such as halo, preferably iodo, under standard Ulman conditions (Fanta, F. E., *Chem. Rev.*, 64, 1964:613) provides indoles of Formula D, wherein $R^{4b}$ is phenoxy and $R^2$ is as defined in Formula I. Preferred conditions are iodobenzene in the presence of potassium carbonate, copper (I) bromide and copper powder in N-methylpyrrolidine at 170° C.

Scheme 5

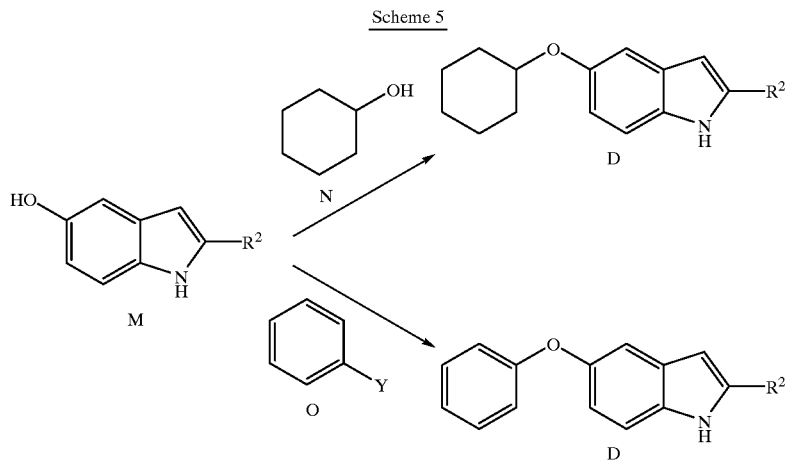

The reactions shown in Schemes 4 and 5 could also be applied to indoles with the 3-position group in place. In some cases, the chemistries outlined above may have to be modified, for instance by use of protecting groups, to prevent side reactions due to reactive groups, such as reactive groups attached as substituents.

In another embodiment of the invention, the present compounds can be used to distinguish 5-$HT_6$ receptors from other receptor subtypes, for example glutamate or opioid receptors, within a population of receptors, and in particular to distinguish between the 5-$HT_6$ and other 5-HT receptor subtypes. The latter can be achieved by incubating preparations of the 5-$HT_6$ receptor and one of the other 5-HT receptor subtypes (for example 5-$HT_{2A}$) with a 5-$HT_6$-selective compound of the invention and then incubating the resulting preparation with a radiolabeled serotonin receptor ligand, for example [$^3$H]-serotonin. The 5-$HT_6$ receptors are then distinguished by determining the difference in membrane-bound activity, with the 5-$HT_6$ receptor exhibiting lesser radioactivity, i.e., lesser [$^3$H]-serotonin binding, than the other 5-HT receptor subtype.

In another embodiment of the invention, the compound is provided in labeled form, such as radiolabeled form, e. g. labeled by incorporation within its structure $^3$H or $^{14}$C or by conjugation to $^{125}$I. In another aspect of the invention, the compounds in labeled form can be used to identify 5-$HT_6$ receptor ligands by techniques common in the art. This can be achieved by incubating the receptor or tissue in the presence of a ligand candidate and then incubating the resulting preparation with an equimolar amount of radiolabeled compound of the invention such as [$^3$H]-5-fluoro-1-(4-methylphenylsulfonyl)-3-(1-methyl-1,2,3,6-tetrahydro-4-pyridinyl)indole. 5-$HT_6$ receptor ligands are thus revealed as those that are not significantly displaced by the radiolabeled compound of the present invention. Alternatively, 5-$HT_6$ receptor ligand candidates may be identified by first incubating a radiolabeled form of a compound of the invention then incubating the resulting preparation in the presence of the candidate ligand. A more potent 5-$HT_6$ receptor ligand will, at equimolar concentration, displace the radiolabeled compound of the invention.

The present compounds are useful as pharmaceuticals for the treatment of various conditions in which the use of a 5-$HT_6$ antagonist is indicated, such as psychosis, schizophrenia, manic depression, depression, neurological disturbances, memory disturbances, Parkinsonism, amylotrophic lateral sclerosis, Alzheimer's disease and Huntington's disease. In another of its aspects, the present invention provides pharmaceutical compositions useful to treat 5-$HT_6$-related medical conditions, in which a compound of Formula I is present in an amount effective to antagonize 5-$HT_6$ receptor stimulation, together with a pharmaceutically acceptable carrier. In a related aspect, the invention provides a method for treating medical conditions for which a 5-$HT_6$ receptor antagonist is indicated, which comprises the step of administering to the patient an amount of a compound of Formula I effective to antagonize 5-$HT_6$ receptor stimulation, an a pharmaceutically acceptable carrier therefor.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal, patch, pump or transdermal administration and the pharmaceutical compositions formulated accordingly.

Compounds of Formula I and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Suitable unit dosages, i.e. therapeutically effective amounts, can be determined during clinical trials designed appropriately for each of the conditions for which administration of a chosen compound is indicated and will of course vary depending on the desired clinical endpoint. Each dosage unit for oral administration may contain from 0.01 to 500 mg/kg (and for parenteral administration may contain from 0.1 to 50 mg) of a compound of Formula I, or a pharmaceutically acceptable salt thereof calculated as the free base, and will be administered in a frequency appropriate for initial and maintenance treatments. For laboratory use, the present compounds can be stored in packaged form for reconstitution and use.

EXPERIMENTAL EXAMPLES

Example 1

5-Cyclohexyloxy-1H-indole

Triphenylphosphine (10.3 g, 39.4 mmol) and 5-hydroxy-1H-indole (5 g, 36.9 mmol) were added to a solution of cyclohexanol (3.7 mL, 35.7 mmol) in THF (200 mL) at 0° C. DEAD (5.9 mL, 39.4 mmol) was slowly added and the resulting solution was stirred for 1 week at room temperature. The solvent was removed in vacuo and flash chromatography (silica gel, 10% ethyl acetate in hexane) yielded 5-cyclohexyloxy-1H-indole (3.2 g, 40%).

Example 2

5-Trifluoromethoxy-1H-indole

Lithium aluminum hydride (10.4 mL, 1M in THF, 10.4 mmol) was added to a solution of 5-trifluoromethoxyisatin (0.8 g, 3.45 mmol) in THF at room temperature and the mixture was refluxed overnight. The reaction mixture was cooled, and $Na_2SO_4 10H_2O$ was added very carefully portionwise, followed by ethyl acetate. The reaction mixture was then filtered, and the filtrate was evaporated. The residual oil was purifed by column chromatography with ethyl acetate in hexanes (2:98) to yield 5-trifluoromethoxy-1H-indole (0.162 g, 23%).

Example 3

5,7-Difluoro-1H-indole

Vinylmagnesium bromide (30 mL, 1M in THF, 30 mmol) was added dropwise to a solution of 2,4-difluoronitrobenzene (1.6 g, 10 mmol) in THF at −40° C. The mixture was stirred for 30 min and then poured into $CH_2Cl_2$-diluted HCl. The organic layer was separated and dried ($Na_2SO_4$). After the solvent was removed in vacuo, the residual oil was purifed by column chromatography with EtOAc/Hexanes (2:98) to yield 2,4-difluoro-1H-indole (189 mg, 12%).

Example 4(a)

5-Bromo-3-(1-methyl-1,2,3,6-tetrahydro-4-pyridinyl)-1H-indole

5-Bromo-1H-indole (4.31 g, 22 mmol), 1-methyl-4-piperidone (2.46 mL, 20 mmol) and pyrrolidine (17 mL, 200 mmol) were mixed in ethanol (30 mL) and refluxed for 72 hours. The mixture was cooled to room temperature and the resulting solid, collected by filtration, washed with methanol and dried to provide the title compound as a white solid (4.40 g, 76%). mp>230° C., dec.

In a like manner, the following additional compounds were prepared:

(b) 5-Fluoro-3-(1-methyl-1,2,3,6-tetrahydro-4-pyridinyl)-1H-indole: from 5-fluoro-1H-indole;

(c) 5-Cyclohexyloxy-3-(1-methyl-1,2,3,6-tetrahydro-4-pyridinyl)-1H-indole: from 5-cyclohexyloxy-1H-indole (Example 1);

(d) 5-Chloro-3-(1-methyl-1,2,3,6-tetrahydro-4-pyridinyl)-1H-indole: from 5-chloro-1H-indole;

(e) 3-(1-methyl-1,2,3,6-tetrahydro-4-pyridinyl)-1H-indole: from 1H-indole;

(f) 6-Bromo-3-(1-methyl-1,2,3,6-tetrahydro-4-pyridinyl)-1H-indole: from 6-bromo-1H-indole;

(g) 5,7-Difluoro-3-(1-methyl-1,2,3,6-tetrahydro-4-pyridinyl)-1H-indole: (176.8 mg, 58%); from 5,7-difluoroindole (Example 3, 188 mg, 1.23 mmol) and N-methyl-4-piperidone (153.4 mg, 1.23 mmol) with pyrrolidine (875 mg, 12.3 mmol) in ethanol (1.5 mL) at reflux. m.p 215–21° C., HRMS-FAB$^+$ for $C_{14}H_{14}N_2F_2$: calc.MH$^+$: 249.12033; found; 249.12095;

(h) 3-(1-Methyl-1,2,3,6-tetrahydro-4-pyridinyl)-5-trifluoromethoxy-1H-indole: from 5-trifluoromethoxy-1H-indole (Example 2);

(i) 3-(1-Methyl-1,2,3,6-tetrahydro-4-pyridinyl)-5-trifluoromethyl-1H-indole: from 5-trifluoromethyl-1H-indole (prepared according to Miyano, et al., JP-60204759);

(j) 6-Chloro-3-(1-methyl-1,2,3,6-tetrahydro-4-pyridinyl)-1H-indole: from 6-chloro-1H-indole.

Example 5(a)

5-Cyclohexyloxy-3-(1-methyl-4-piperidinyl)-1H-indole

Palladium on carbon (10%, 31 mg) was added to a solution of 5-cyclohexyloxy-3-(1-methyl-1,2,3,6- tetrahydro-4-pyridinyl)-1H-indole (Example 4c, 48.4 mg, 0.16 mmol) in methanol (5 mL) and the mixture was stirred under an atmosphere of hydrogen for 8 h. Removal of the catalyst by filtration through celite and silica (20% 2M methanolic ammonia in dichloromethane) yielded 5-cyclohexyloxy-3-(1-methyl-4-piperidinyl)-1H-indole (quantitative, HRMS-FAB$^+$ for $C_{20}H_{28}N_2O$: calculated MH+: 313.22800; found MH$^+$: 313.23083).

In a like manner, the following additional compounds were prepared:

(b) 6-Chloro-3-(1-methyl-4-piperidinyl)-1H-indole: (0.815 g, 81%); from 6-chloro-3-(1-methyl-1,2,3,6-tetrahydro-4-pyridinyl)-1H-indole (Example 4j, 1.0 g, 4 mmol) and 5% Pt/C (0.78 g, 0.2 mmol) in ethanol under H$_2$; m.pt. 218–24° C.

(c) 5-Fluoro-3-(1-methyl-4-piperidinyl)-1H-indole: (0.64 g, 64%); from 5-fluoro-3-(1-methyl-1,2,3,6-tetrahydro-4-pyridinyl)-1H-indole (Example 4b, 1.0 g, 4.34 mmol) and 5% Pt/C(0.43 g, 0.4 mmol) in ethanol under H$_2$; mp 158–61° C. HRMS-FAB$^+$ for $C_{14}H_{17}N_2F$ caculated MH+: 233.14540, found: 233.13193.

(d) 3-(1-Methyl-4-piperidinyl)-1H-indole: (0.92 g, 91%); from 3-(1-methyl-1,2,3,6-tetrahydro-4-pyridinyl)-1H-indole (Example 4e, 1.0 g,4.69 mmol) and 10% Pd/C on carbon (0.5 g, 0.47 mmol) in ethanol under H$_2$; mp 174–6° C.; HRMS-FAB$^+$ for $C_{14}H_{18}N_2$, caculated MH+: 215.15483, found: 215.15356.

(e) 5-Chloro-3-(1-methyl-4-piperidinyl)indole: (0.89 g, 88%); from 5-chloro-3-(1-methyl-1,2,3,6-tetrahydro-4-pyridinyl)indole (Example 4d, 1.0 g, 4 mmol) and 5% Pt/C (0.78 g, 0.2 mmol) in methanol under H$_2$; mp 192–4° C.; HRMS-FAB$^+$ for $C_{14}H_{17}N_2Cl$ calculated MH+: 249.11584, found: 249.11529.

Example 6(a)

1-Benzoyl-5-fluoro-3-(1-methyl-1,2,3,6-tetrahydro-4-pyridinyl)indole

Benzoyl chloride (33.3 mg, 0.24 mmol) was added to a solution of 5-fluoro-3-(1-methyl-1,2,3,6-tetrahydro-4-pyridinyl)indole (Example 4b, 49.6 mg, 0.215 mmol), triethylamine (0.15 mL, 1.1 mmol) and DMAP (5 mg) in dichloromethane (2 mL). The mixture was stirred at room temperature prior to quenching with water and extraction into dichloromethane. The organic layer was washed with brine and dried over sodium sulfate. Purification by flash chromatography (silica gel, 2M methanolic ammonia in chloroform) yielded 1-benzoyl-5-fluoro-3-(1-methyl-1,2,3, 6-tetrahydro-4-pyridinyl)indole (27.8 mg, 39%, HRMS-FAB$^+$ for $C_{21}H_{20}N_2OF$ calculated MH$^+$: 335.15598; found: 335.15457).

In a like manner, the following additional compounds were prepared:

(b) 5-Fluoro-1-(4-methylphenylsulfonyl)-3-(1-methyl-1, 2,3,6-tetrahydro-4-pyridinyl)indole: (7.2 mg, 8%), from 5-fluoro-3-(1-methyl-1,2,3,6-tetrahydro-4-pyridinyl)indole (Example 4b, 52.0 mg, 0.226 mmol) and 4-methylphenylsulfonyl chloride (48.0 mg, 0.25 mmol); HRMS-FAB$^+$ for $C_{21}H_{22}N_2O_2SF$: calculated MH$^+$: 385.13861; found: 385.14053.

(c) 1-(2-Chlorobenzoyl)-5-fluoro-3-(1-methyl-1,2,3,6-tetrahydro-4-pyridinyl)indole: (21 mg, 34%), from 5-fluoro-3-(1-methyl-1,2,3,6-tetrahydro-4-pyridinyl) indole (Example 4b, 37.2 mg, 0.62 mmol) and 2-chlorobenzoyl chloride (28.3 mg, 0.19 mmol); HRMS-FAB$^+$ for $C_{21}H_{19}N_2OClF$: calculated MH$^+$ 369.11700; found: 369.11418.

(d) 5-Fluoro-1-(4-methoxybenzoyl)-3-(1-methyl-1,2,3,6-tetrahydro-4-pyridinyl)indole: (30.2 mg, 64%), from 5-fluoro-3-(1-methyl-1,2,3,6-tetrahydro-4-pyridinyl) indole (Example 4b, 29.9 mg, 0.15 mmol) and 4-methoxybenzoyl chloride (22.2 mg, 0.16 mmol); HRMS-FAB$^+$ for $C_{22}H_{22}N_2O_2F$: calculated MH$^+$: 365.16653; found: 365.16747.

(e) 5-Fluoro-1-(3,4-methylenedioxybenzoyl)-3-(1-methyl-1,2,3,6-tetrahydro-4-pyridinyl)indole: (11.1 mg, 20%), from 5-fluoro-3-(1-methyl-1,2,3,6-tetrahydro-4-pyridinyl)indole (Example 4b, 33.8 mg, 0.147 mmol) and 3,4-methylenedioxybenzoyl chloride (27.1 mg, 0.176 mmol); HRMS-FAB$^+$ for $C_{22}H_{20}N_2O_3F$ calculated MH$^+$: 379.14578; found: 379.14399.

(f) 1-(2,6-Dichlorobenzoyl)-5-fluoro-3-(1-methyl-1,2,3, 6-tetrahydro-4-pyridinyl)indole: (20.6 mg, 32%), from 5-fluoro-3-(1-methyl-1,2,3,6-tetrahydro-4-pyridinyl) indole (Example 4b, 36.8 mg, 0.160 mmol) and 2,6-dichlorobenzoyl chloride (33.5 mg, 0.19 mmol); HRMS-FAB$^+$ for $C_{21}H_{18}N_2OCl_2F$ calculated MH$^+$: 403.07803; found: 403.08101.

(g) 1-Benzoyl-5-bromo-3-(1-methyl-1,2,3,6-tetrahydro-4-pyridinyl)indole: (442 mg, 65%), from 5-bromo-3-(1-methyl-1,2,3,6-tetrahydro-4-pyridinyl)indole (Example 4a, 500 mg, 1.72 mmol) and benzoyl chloride (239 μL, 2.06 mmol).

Example 7(a)

3-(1-Methyl-1,2,3,6-tetrahydro-4-pyridinyl)-1-phenylsulfonylindole

Sodium bis(trimethylsilyl)amide (0.23 mL, 1M inTHF, 0.23 mmol) was added to a solution of 3-(1-methyl-1,2,3, 6-tetrahydro-4-pyridinyl)indole (Example 4e, 25.0 mg, 0.12 mmol) in THF (1.5 mL) at −78° C. and the mixture was stirred for 1 h. Phenylsulfonyl chloride (30 uL, 0.24 mmol) was added and the mixture stirred at room temperature for 2 h. prior to quenching with water (4 drops) and silica gel (~1g). Purification using solid phase extraction tubes (1000 mg silica, eluting with 0–10% 2M methanolic ammonia in dichloromethane) yielded 3-(1-methyl-1,2,3,6-tetrahydro-4-pyridinyl)-1-phenylsulfonylindole (9.0 mg, 22%, HRMS-FAB$^+$ for $C_{20}H_{20}N_2O_2S$: calculated MH$^+$: 353.13239; found: 353.13235).

In a like manner, the following additional compounds were prepared:

(b) 1-(4-Methoxyphenylsulfonyl)-3-(1-methyl-1,2,3,6-tetrahydro-4-pyridinyl)indole: (9.0 mg, 20%); from 3-(1-methyl-1,2,3,6-tetrahydro-4-pyridinyl)-1H-indole (Example 4e, 24.8 mg, 0.12 mmol) and 4-methoxyphenylsulfonyl chloride (48.2 mg, 0.23 mmol); HRMS-FAB$^+$ for $C_{21}H_{22}N_2O_3S$: calculated MH$^+$: 383.14294; found: 383.14276.

(c) 1-(4-Fluorophenylsulfonyl)-3-(1-methyl-1,2,3,6-tetrahydro-4-pyridinyl)indole: (9.0 mg, 21%); from 3-(1-methyl-1,2,3,6-tetrahydro-4-pyridinyl)-1H-indole (Example 4e, 24.8 mg, 0.12 mmol) and 4-fluorophenylsulfonyl chloride (46.5 mg, 0.24 mmol); HRMS-FAB$^+$ for $C_{20}H_{19}N_2O_2SF$: calculated MH$^+$: 371.12296; found: 371.12323.

(d) 1-(4-Bromophenylsulfonyl)-5-fluoro-3-(1-methyl-1, 2,3,6-tetrahydro-4-pyridinyl)indole: (43.8 mg, 90%);

from 5-fluoro-3-(1-methyl-1,2,3,6-tetrahydro-4-pyridinyl)-1H-indole (Example 4b, 25.0 mg, 0.108 mmol) and 4-bromophenylsulfonyl chloride (56.4 mg, 0.22 mmol); HRMS-FAB$^+$ for $C_{20}H_{18}N_2O_2SFBr$: calculated MH$^+$: 449.03348; found: 449.03297.

(e) 5-Fluoro-1-(2,5-dichlorophenylsulfonyl)-3-(1-methyl-1,2,3,6-tetrahydro-4-pyridinyl)indole: (36.5 mg, 76%); from 5-fluoro-3-(1-methyl-1,2,3,6-tetrahydro-4-pyridinyl)-1H-indole (Example 4b, 25.3 mg, 0.110 mmol) and 2,5-dichlorophenylsulfonyl chloride (55.6 mg, 0.23 mmol); HRMS-FAB$^+$ for $C_{20}H_{17}N_2O_2SFCl_2$: calculated MH$^+$: 439.04501; found: 439.04294.

(f) 1-(4-Chloro-3-nitrophenylsulfonyl)-5-fluoro-3-(1-methyl-1,2,3,6-tetrahydro-4-pyridinyl)indole: (39.1 mg, 79%); from 5-fluoro-3-(1-methyl-1,2,3,6-tetrahydro-4-pyridinyl)-1H-indole (Example 4b, 25.4 mg, 0.110 mmol) and 4-chloro-3-nitrophenylsulfonyl chloride (57.6 mg, 0.22 mmol); HRMS-FAB$^+$ for $C_{20}H_{17}N_2O_4SFCl$: calculated MH$^+$: 450.06906; found: 450.07176.

(g) 5-Fluoro-3-(1-methyl-1,2,3,6-tetrahydro-4-pyridinyl)-1-(2,4,6-trimethylphenylsulfonyl)indole: (34.7 mg, 76%); from 5-fluoro-3-(1-methyl-1,2,3,6-tetrahydro-4-pyridinyl)-1H-indole (Example 4b, 25.5 mg, 0.110 mmol) 2,4,6-trimethylphenylsulfonyl chloride (48.4 mg, 0.22 mmol); HRMS-FAB$^+$ for $C_{23}H_{25}N_2O_2SF$: calculated MH$^+$: 413.16989; found: 413.17396.

(h) 5-Fluoro-3-(1-methyl-1,2,3,6-tetrahydro-4-pyridinyl)-1-(2,4,6-triisopropylphenylsulfonyl)indole: (25.8 mg, 48%); from 5-fluoro-3-(1-methyl-1,2,3,6-tetrahydro-4-pyridinyl)-1H-indole (Example 4b, 24.9 mg, 0.108 mmol) 2,4,6-triisopropylphenylsulfonyl chloride (68.8 mg, 0.23 mmol); HRMS-FAB$^+$ for $C_{29}H_{37}N_2O_2SF$: calculated MH$^+$: 497.26379; found: 497.26112.

(i) 5-Cyclohexyloxy-1-(4-methylphenylsulfonyl)-3-(1-methyl-1,2,3,6-tetrahydro-4-pyridinyl)indole: (49.0 mg, 94%); from 5-cyclohexyloxy-3-(1-methyl-1,2,3,6-tetrahydro-4-pyridinyl)-1H-indole (Example 4c, 35.0 mg, 0.112 mmol) and 4-methylphenylsulfonyl chloride (41 mg, 0.22 mmol); HRMS-FAB$^+$ for $C_{27}H_{32}N_2O_3S$: calculated MH$^+$: 465.22119; found: 465.22309.

(j) 6-Bromo-3-(1-methyl-1,2,3,6-tetrahydro-4-pyridinyl)-1-phenylsulfonylindole: (23.9 mg, 64%); from 6-bromo-3-(1-methyl-1,2,3,6-tetrahydro-4-pyridinyl)-1H-indole (Example 4f, 25.0 mg, 0.086 mmol) and phenylsulfonyl chloride (22 uL, 0.17 mmol); HRMS-FAB$^+$ for $C_{20}H_{19}N_2O_2BrS$: calculated MH$^+$: 431.04288; found: 431.04656.

(k) 6-Bromo-1-(4-methoxyphenylsulfonyl)-3-(1-methyl-1,2,3,6-tetrahydro-4-pyridinyl)indole: (24.5 mg, 62%); from 6-bromo-3-(1-methyl-1,2,3,6-tetrahydro-4-pyridinyl)1H-indole (Example 4f, 25.0 mg, 0.086 mmol) and 4-methoxyphenylsulfonyl chloride (35 mg, 0.17 mmol); HRMS-FAB$^+$ for $C_{21}H_{21}N_2O_3BrS$: calculated MH$^+$: 461.05344; found: 461.04886.

(l) 6-Bromo-1-(4-fluorophenylsulfonyl)-3-(1-methyl-1,2,3,6-tetrahydro-4-pyridinyl)-indole: (20.9 mg, 54%); from 6-bromo-3-(1-methyl-1,2,3,6-tetrahydro-4-pyridinyl)-1H-indole (Example 4f, 25.1 mg, 0.086 mmol) and 4-fluorophenylsulfonyl chloride (35 mg, 0.18 mmol); HRMS-FAB$^+$ for $C_{20}H_{18}N_2O_2BrSF$: calculated MH$^+$: 449.03348; found: 449.02907.

(m) 5-Cyclohexyloxy-3-(1-methyl-1,2,3,6-tetrahydro-4-pyridinyl)-1-phenylsulfonylindole: (34.1 mg, 92%); from 5-cyclohexyloxy-3-(1-methyl-1,2,3,6-tetrahydro-4-pyridinyl)-1H-indole (Example 4c, 25.6 mg, 0.082 mmol) and phenylsulfonyl chloride (20 uL, 0.157 mmol); HRMS-FAB$^+$ for $C_{26}H_{30}N_2O_3S$: calculated MH$^+$: 451.20554; found: 451.20922.

(n) 5-Cyclohexyloxy-3-(1-methyl-1,2,3,6-tetrahydro-4-pyridinyl)-1-(1-naphthylsulfonyl)indole: (35.9 mg, 87%); from 5-cyclohexyloxy-3-(1-methyl-1,2,3,6-tetrahydro-4-pyridinyl)-1H-indole (Example 4c, 25.5 mg, 0.082 mmol) and 1-naphthylsulfonyl chloride (37.7 mg, 0.17 mmol); HRMS-FAB$^+$ for $C_{30}H_{32}N_2O_3S$: calculated MH$^+$: 501.22119; found: 501.21807.

(o) 5-Cyclohexyloxy-3-(1-methyl-1,2,3,6-tetrahydro-4-pyridinyl)-1-(2-naphthylsulfonyl)indole: (37.4 mg, 92%); from 5-cyclohexyloxy-3-(1-methyl-1,2,3,6-tetrahydro-4-pyridinyl)-1H-indole (Example 4c, 25.2 mg, 0.081 mmol) and 2-naphthylsulfonyl chloride (38.5 mg, 0.17 mmol); HRMS-FAB$^+$ for $C_{30}H_{32}N_2O_3S$: calculated MH$^+$: 501.22119; found: 501.22101.

(p) 1-(2-Bromophenysulfonyl)-5-cyclohexyloxy-3-(1-methyl-1,2,3,6-tetrahydro-4-pyridinyl)indole: (34.4 mg, 82%); from 5-cyclohexyloxy-3-(1-methyl-1,2,3,6-tetrahydro-4-pyridinyl)-1H-indole (Example 4c, 24.5 mg, 0.079 mmol) and 2-bromophenylsulfonyl chloride (40.2 mg, 0.16 mmol); HRMS-FAB$^+$ for $C_{26}H_{29}N_2O_3SBr$: calculated MH$^+$: 529.11603; found: 529.11380.

(q) 5-Cyclohexyloxy-1-(2,5-dichlorophenylsulfonyl)-3-(1-methyl-1,2,3,6-tetrahydro-4-pyridinyl)indole: (37.3 mg, 89%); from 5-cyclohexyloxy-3-(1-methyl-1,2,3,6-tetrahydro-4-pyridinyl)-1H-indole (Example 4c, 25.5 mg, 0.082 mmol) and 2,5-dichlorophenylsulfonyl chloride (42.0 mg, 0.17 mmol); HRMS-FAB$^+$ for $C_{26}H_{28}N_2O_3SCl_2$: calculated MH$^+$: 519.12762; found: 519.12579.

(r) 5-Cyclohexyloxy-3-(1-methyl-1,2,3,6-tetrahydro-4-pyridinyl)-1-(2,4,6-trimethylphenylsulfonyl)indole: (31.6 mg, 78%); from 5-cyclohexyloxy-3-(1-methyl-1,2,3,6-tetrahydro-4-pyridinyl)-1H-indole (Example 4c, 25.5 mg, 0.082 mmol) 2,4,6-trimethylphenylsulfonyl chloride (36.8 mg, 0.17 mmol); HRMS-FAB$^+$ for $C_{29}H_{36}N_2O_3S$: calculated MH$^+$: 493.25250; found: 493.25329.

(s) 5-Cyclohexyloxy-3-(1-methyl-1,2,3,6-tetrahydro-4-pyridinyl)-1-(2,4,6-triisopropylphenylsulfonyl)indole: (23.3 mg, 50%); from 5-cyclohexyloxy-3-(1-methyl-1,2,3,6-tetrahydro-4-pyridinyl)-1H-indole (Example 4c, 25.2 mg, 0.081 mmol) 2,4,6-triisopropylphenylsulfonyl chloride (53.7 mg, 0.18 mmol); HRMS-FAB$^+$ for $C_{35}H_{48}N_2O_3S$: calculated MH$^+$: 577.34637; found: 577.34710.

(t) 5-Cyclohexyloxy-3-(1-methyl-1,2,3,6-tetrahydro-4-pyridinyl)-1-(3-nitrophenylsulfonyl)indole: (38.0 mg, 96%); from 5-cyclohexyloxy-3-(1-methyl-1,2,3,6-tetrahydro-4-pyridinyl)-1H-indole (Example 4c, 24.8 mg, 0.080 mmol) and 3-nitrophenylsulfonyl chloride (35.3 mg, 0.159 mmol); HRMS-FAB$^+$ for $C_{26}H_{29}N_3O_5S$: calculated MH$^+$: 496.19061; found: 496.19042.

(u) 1-(4-Chloro-3-nitrophenylsulfonyl)-5-cyclohexyloxy-3-(1-methyl-1,2,3,6-tetrahydro-4-pyridinyl)indole: (37.4 mg, 87%); from 5-cyclohexyloxy-3-(1-methyl-1,2,3,6-tetrahydro-4-pyridinyl)-1H-indole (Example 4c, 25.1 mg, 0.081 mmol) and 4-chloro-3-nitrophenylsulfonyl chloride (42.7 mg, 0.17 mmol); HRMS-FAB$^+$ for $C_{26}H_{28}N_3O_5SCl$: calculated MH$^+$: 530.15167; found: 530.14727.

(v) 5-Cyclohexyloxy-3-(1-methyl-1,2,3,6-tetrahydro-4-pyridinyl)-1-(3-nitro-4-trifluoromethylphenylsulfonyl) indole: (33.9 mg, 75%); from 5-cyclohexyloxy-3-(1-methyl-1,2,3,6-tetrahydro-4-pyridinyl)-1H-indole (Example 4c, 24.8 mg, 0.080 mmol) and 3-nitro-4-trifluoromethylphenylsulfonyl chloride (48.4 mg, 0.167 mmol); HRMS-FAB$^+$ for $C_{27}H_{28}N_3O_5SF_3$: calculated MH$^+$: 564.17798; found: 564.17855.

(w) 1-(4-Bromophenylsulfonyl)-5-cyclohexyloxy-3-(1-methyl-1,2,3,6-tetrahydro-4-pyridinyl)indole: (31.4 mg, 72%); from 5-cyclohexyloxy-3-(1-methyl-1,2,3,6-tetrahydro-4-pyridinyl)-1H-indole (Example 4c, 25.7 mg, 0.083 mmol) and 4-bromophenylsulfonyl chloride (43 mg, 0.17 mmol); HRMS-FAB$^+$ for $C_{26}H_{29}N_2O_3SBr$: calculated MH$^+$: 529.11603; found: 529.11817.

(x) 5-Cyclohexyloxy-1-(4-methoxyphenylsulfonyl)-3-(1-methyl-1,2,3,6-tetrahydro-4-pyridinyl)indole: (34.8 mg, 89%); from 5-cyclohexyloxy-3-(1-methyl-1,2,3,6-tetrahydro-4-pyridinyl)-1H-indole (Example 4c, 25.2 mg, 0.081 mmol) and 4-methoxyphenylsulfonyl chloride (34.1 mg, 0.165 mmol); HRMS-FAB$^+$ for $C_{27}H_{32}N_2O_4S$: calculated MH$^+$: 481.21609; found: 481.21625.

(y) 5-Cyclohexyloxy-1-(4-fluorophenylsulfonyl)-3-(1-methyl-1,2,3,6-tetrahydro-4-pyridinyl)indole: (34.0 mg, 88%); from 5-cyclohexyloxy-3-(1-methyl-1,2,3,6-tetrahydro-4-pyridinyl)-1H-indole (Example 4c, 25.5 mg, 0.082 mmol) and 4-fluorophenylsulfonyl chloride (30.8 mg, 0.16 mmol); HRMS-FAB$^+$ for $C_{26}H_{29}N_2O_3SF$: calculated MH$^+$: 469.19611; found: 469.19626.

(z) 1-(4-Chlorophenylsulfonyl)-5-cyclohexyloxy-3-(1-methyl-1,2,3,6-tetrahydro-4-pyridinyl)indole: (37.7 mg, 94%); from 5-cyclohexyloxy-3-(1-methyl-1,2,3,6-tetrahydro-4-pyridinyl)-1H-indole (Example 4c, 25.5 mg, 0.082 mmol) and 4-chlorophenylsulfonyl chloride (35.6 mg, 0.169 mmol); HRMS-FAB$^+$ for $C_{26}H_{29}N_2O_3SCl$: calculated MH$^+$: 485.16656; found: 485.16480.

(aa) 1-(4-t-Butylphenylsulfonyl)-5-cyclohexyloxy-3-(1-methyl-1,2,3,6-tetrahydro-4-pyridinyl)indole: (34.0 mg, 81%); from 5-cyclohexyloxy-3-(1-methyl-1,2,3,6-tetrahydro-4-pyridinyl)-1H-indole (Example 4c, 25.6 mg, 0.082 mmol) and 4-t-butylphenylsulfonyl chloride (37.2 mg, 0.16 mmol); HRMS-FAB$^+$ for $C_{30}H_{38}N_2O_3S$: calculated MH$^+$: 507.26813; found: 507.27183.

(bb) 1-(2-Bromophenylsulfonyl)-5-fluoro-3-(1-methyl-1,2,3,6-tetrahydro-4-pyridinyl)indole: (32 mg, 53%), from 5-fluoro-3-(1-methyl-1,2,3,6-tetrahydro-4-pyridinyl)-1H-indole (Example 4b, 30.6 mg, 0.133 mmol) and 2-bromophenylsulfonyl chloride (67.9 mg, 0.27 mmol); HRMS-FAB$^+$ for $C_{20}H_{19}N_2SO_2BrF$: calculated MH$^+$: 449.03348; found: 449.03240.

(cc) 1-(4-Fluorophenylsulfonyl)-5-fluoro-3-(1-methyl-1,2,3,6-tetrahydro-4-pyridinyl)indole: (30 mg, 57%), from 5-fluoro-3-(1-methyl-1,2,3,6-tetrahydro-4-pyridinyl)-1H-indole (Example 4b) and 4-fluorophenylsulfonyl chloride (52.9 mg, 0.27 mmol); HRMS-FAB$^+$ for $C_{20}H_{19}N_2O_2SF_2$ calculated MH$^+$: 389.11353; found: 389.11544.

(dd) 1-(4-Chlorophenylsulfonyl)-5-fluoro-3-(1-methyl-1,2,3,6-tetrahydro-4-pyridinyl)indole: (28.1 mg, 53%), from 5-fluoro-3-(1-methyl-1,2,3,6-tetrahydro-4-pyridinyl)-1H-indole (Example 4b, 30.1 mg, 0.131 mmol) and 4-chlorophenylsulfonyl chloride (55.3 mg, 0.26 mmol); HRMS-FAB$^+$ for $C_{20}H_{19}N_2O_2SClF$ calculated MH$^+$: 405.08998; found: 405.08291.

(ee) 1-(4-t-Butylphenylsulfonyl)-5-fluoro-3-(1-methyl-1,2,3,6-tetrahydro-4-pyridinyl)indole: (23.0 mg, 42%), from 5-fluoro-3-(1-methyl-1,2,3,6-tetrahydro-4-pyridinyl)-1H-indole (Example 4b, 29.4 mg, 0.128 mmol) and 4-t-butylphenylsulfonyl chloride (59.6 mg, 0.26 mmol); HRMS-FAB$^+$ for $C_{24}H_{28}N_2O_2SF$ calculated MH$^+$: 427.18555; found: 427.18680.

(ff) 5-Fluoro-3-(1-methyl-1,2,3,6-tetrahydro-4-pyridinyl)-1-(3-nitrophenylsulfonyl)indole: (31.0 mg, 56%), from 5-fluoro-3-(1-methyl-1,2,3,6-tetrahydro-4-pyridinyl)-1H-indole (Example 4b, 30.1 mg, 0.131 mmol) and 3-nitrophenylsulfonyl chloride (58.1 mg, 0.26 mmol); HRMS-FAB$^+$ for $C_{20}H_{19}N_3O_4SF$ calculated MH$^+$: 416.10803; found: 416.10631.

(gg) 5-Fluoro-3-(1-methyl-1,2,3,6-tetrahydro-4-pyridinyl)-1-(1-naphthylsulfonyl)indole: (28.2 mg, 52%), from 5-fluoro-3-(1-methyl-1,2,3,6-tetrahydro-4-pyridinyl)-1H-indole (Example 4b, 29.4 mg, 0.128 mmol) and 1-naphthylsulfonyl chloride (58 mg, 0.26 mmol); HRMS-FAB$^+$ for $C_{24}H_{22}N_2O_2SF$ calculated MH$^+$: 421.13861; found: 421.14099.

(hh) 5-Fluoro-3-(1-methyl-1,2,3,6-tetrahydro-4-pyridinyl)-1-(2-naphthylsulfonyl)indole: (32.3 mg, 56%), from 5-fluoro-3-(1-methyl-1,2,3,6-tetrahydro-4-pyridinyl)-1H-indole (Example 4b, 31.4 mg, 0.136 mmol) and 2-naphthylsulfonyl chloride (61.7 mg, 0.27 mmol); HRMS-FAB$^+$ for $C_{24}H_{22}N_2O_2SF$ calculated MH$^+$: 421.13861; found: 421.13866.

(ii) 5-Fluoro-3-(1-methyl-1,2,3,6-tetrahydro-4-pyridinyl)-1-phenylsulfonylindole: (28.2 mg, 60%), from 5-fluoro-3-(1-methyl-1,2,3,6-tetrahydro-4-pyridinyl)-1H-indole (Example 4b, 29.5 mg, 0.128 mmol) and phenylsulfonyl chloride (45.3 mg, 0.26 mmol); HRMS-FAB$^+$ for $C_{20}H_{20}N_2O_2SF$ calculated MH$^+$: 371.12296; found: 371.12242.

(jj) 5-Chloro-3-(1-methyl-1,2,3,6-tetrahydro-4-pyridinyl)-1-phenylsulfonylindole: from 5-chloro-3-(1-methyl-1,2,3,6-tetrahydro-4-pyridinyl)-1H-indole (Example 4d, 25 mg, 0.10 mmol) and phenylsulfonyl chloride (26.4 mg, 0.15 mmol). The HCl salt (29.5 mg, 70%) was prepared from the crude product using 1M HCl in ether; m.p 245–8° C., HRMS-FAB$^+$ for $C_{20}H_{19}N_2O_2SCl.HCl$, calculated MH$^+$(—HCl): 387.09341; found: 387.09262.

(kk) 5-Chloro-1-(4-fluorophenylsulfonyl)-3-(1-methyl-1,2,3,6-tetrahydro-4-pyridinyl)indole: from 5-chloro-3-(1-methyl-1,2,3,6-tetrahydro-4-pyridinyl)-1H-indole (Example 4d, 25 mg, 0.1 mmol) and 4-fluorophenylsulfonyl chloride (29.1 mg, 0.15 mmol). The HCl salt ether (32.6 mg, 74%) was prepared from the crude product using 1M HCl in ether. m.p 256–7° C., HRMS-FAB$^+$ for $C_{20}H_{18}N_2O_2SClF.HCl$, calculated MH$^+$(—HCl): 405.08398; found: 405.0797.

(ll) 3-(1-Methyl-1,2,3,6-tetrahydro-4-pyridinyl)-1-phenylsulfonyl-5-trifluoromethoxyindole: from 3-(1-methyl-1,2,3,6-tetrahydro-4-pyridinyl)-5-trifluoromethoxy-1H-indole (Example 4h, 20 mg, 0.068 mmol) and phenylsulfonyl chloride (18.9 mg, 0.11 mmol). The HCl salt (16.7 mg, 50%) was prepared from the crude product using 1M HCl in ether. HRMS-FAB$^+$ for $C_{21}H_{19}N_2O_3SF_3.HCl$, calculated MH$^+$(—HCl): 437.11469; found: 437.11460.

(mm) 1-(4-Fluorophenylsulfonyl)-3-(1-methyl-1,2,3,6-tetrahydro-4-pyridinyl)-5-trifluoromethoxyindole:

from 3-(1-methyl-1,2,3,6-tetrahydro-4-pyridinyl)-5-trifluoromethoxy-1H-indole (Example 4h, 20 mg, 0.068 mmol) and 4-fluorophenylsulfonyl chloride (20.8 mg, 0.11 mmol). The HCl salt (24.0 mg, 69%) was prepared from the crude product using 1M HCl in ether. HRMS-FAB⁺ for $C_{21}H_{18}N_2O_3SF_4 \cdot HCl$, calculated MH⁺(—HCl): 455.10526; found: 455.10735.

(nn) 1-(4-t-Butylphenylsulfonyl)-3-(1-methyl-1,2,3,6-tetrahydro-4-pyridinyl)-5-trifluoromethoxyindole: from 3-(1-methyl-1,2,3,6-tetrahydro-4-pyridinyl)-5-trifluoromethoxy-1H-indole (Example 4h, 20 mg, 0.068 mmol) and 4-t-butylphenylsulfonyl chloride (24.9 mg, 0.11 mmol). The HCl salt (9.4 mg, 25%) was prepared from the crude product using 1M HCl in ether. HRMS-FAB⁺ for $C_{25}H_{27}N_2O_3SF_3 \cdot HCl$, calculated MH⁺(—HCl): 493.17728; found: 493.17565.

(oo) 1-(4-Chlorophenylsulfonyl)-3-(1-methyl-1,2,3,6-tetrahydro-4-pyridinyl)-5-trifluoromethoxyindole: from 3-(1-methyl-1,2,3,6-tetrahydro-4-pyridinyl)-5-trifluoromethoxy-1H-indole (Example 4h, 20 mg, 0.068 mmol) and 4-chlorophenylsulfonyl chloride (22.5 mg, 0.11 mmol). The HCl salt (21.8 mg, 60%) was prepared from the crude product using 1M HCl in ether. HRMS-FAB⁺ for $C_{21}H_{18}N_2O_3SClF_3 \cdot HCl$, calculated MH⁺(—HCl): 473.07275; found: 473.07154.

(pp) 1-(4-Methylphenylsulfonyl)-3-(1-methyl-1,2,3,6-tetrahydro-4-pyridinyl)-5-trifluoromethoxyindole: from 3-(1-methyl-1,2,3,6-tetrahydro-4-pyridinyl)-5-trifluoromethoxy-1H-indole (Example 4h, 20 mg, 0.068 mmol) and 4-methylphenylsulfonyl chloride (20.4 mg, 0.11 mmol). The HCl salt (17.0 mg, 49%) was prepared from the crude product using 1M HCl in ether. HRMS-FAB⁺ for $C_{22}H_{21}N_2O_3SF_3 \cdot HCl$, calculated MH⁺(—HCl): 451.13031; found: 451.12820.

(qq) (4-Methoxyphenylsulfonyl)-3-(1-methyl-1,2,3,6-tetrahydro-4-pyridinyl)-5-trifluoromethoxyindole: from 3-(1-methyl-1,2,3,6-tetrahydro-4-pyridinyl)-5-trifluoromethoxy-1H-indole (Example 4h, 20 mg, 0.068 mmol) and 4-methoxyphenylsulfonyl chloride (22.1 mg, 0.11 mmol). The HCl salt (15.8 mg, 44%) was prepared from the crude product using 1M HCl in ether. HRMS-FAB⁺ for $C_{22}H_{21}N_2O_4SF_3 \cdot HCl$, calculated MH⁺(—HCl): 467.12524; found: 467.12526.

(rr) 3-(1-Methyl-1,2,3,6-tetrahydro-4-pyridinyl)-1-phenylsulfonyl-5-trifluoromethylindole hydrochloride: (14.9 mg, 46%); from 3-(1-methyl-1,2,3,6-tetrahydro-4-pyridinyl)-5-trifluoromethyl-1H-indole (Example 4i, 20 mg, 0.071 mmol) and phenylsulfonyl chloride (18.9 mg, 0.107 mmol). HRMS-FAB⁺ for $C_{21}H_{19}N_2O_2SF_3 \cdot HCl$, calculated MH⁺(—HCl): 421.11975; found: 421.11923.

(ss) 1-(4-Fluorophenylsulfonyl)-3-(1-methyl-1,2,3,6-tetrahydro-4-pyridinyl)-5-trifluoromethylindole hydrochloride: (15.0 mg, 44%); from 3-(1-methyl-1,2,3,6-tetrahydro-4-pyridinyl)-5-trifluoromethyl-1H-indole (Example 4i, 20 mg, 0.071 mmol) and 4-fluorophenylsulfonyl chloride (20.8 mg, 0.107 mmol). HRMS-FAB⁺ for $C_{21}H_{18}N_2O_2SF_4 \cdot HCl$, calculated MH⁺(—HCl): 439.11035; found: 439.10807.

(tt) 1-(4-t-Butylphenylsulfonyl)-3-(1-methyl-1,2,3,6-tetrahydro-4-pyridinyl)-5-trifluoromethylindole hydrochloride: (8.7 mg, 24%); from 3-(1-methyl-1,2,3,6-tetrahydro-4-pyridinyl)-5-trifluoromethyl-1H-indole (Example 4i, 20 mg, 0.071 mmol) and 4-t-butylphenylsulfonyl chloride (24.9 mg, 0.11 mmol). HRMS-FAB⁺ for $C_{25}H_{27}N_2O_2SF_3 \cdot HCl$, calculated MH⁺(—HCl): 477.18237; found: 477.18134.

(uu) 1-(4-Chlorophenylsulfonyl)-3-(1-methyl-1,2,3,6-tetrahydro-4-pyridinyl)-5-trifluoromethylindole hydrochloride: (11.5 mg, 33%); from 3-(1-methyl-1,2,3,6-tetrahydro-4-pyridinyl)-5-trifluoromethyl-1H-indole (Example 4i, 20 mg, 0.071 mmol) and 4-chlorophenylsulfonyl chloride (22.5 mg, 0.11 mmol). HRMS-FAB⁺ for $C_{21}H_{18}ClF_3N_2O_2S \cdot HCl$, calculated MH⁺(—HCl): 455.08078; found: 455.08266.

(vv) 1-(4-Methoxyphenylsulfonyl)-3-(1-methyl-1,2,3,6-tetrahydro-4-pyridinyl)-5-trifluoromethylindole hydrochloride: (22.2 mg, 69%); from 3-(1-methyl-1,2,3,6-tetrahydro-4-pyridinyl)-5-trifluoromethyl-1H-indole (Example 4i, 20 mg, 0.071 mmol) and 4-methoxyphenylsulfonyl chloride (22.1 mg, 0.107 mmol). HRMS-FAB⁺ for $C_{22}H_{21}N_2O_3SF_3 \cdot HCl$, calculated MH⁺: 451.13031; found: 451.13007.

(ww) 1-(4-Methylphenylsulfonyl)-3-(1-methyl-1,2,3,6-tetrahydro-4-pyridinyl)-5-trifluoromethylindole hydrochloride: (14.8 mg, 48%); from 3-(1-methyl-1,2,3,6-tetrahydro-4-pyridinyl)-5-trifluoromethyl-1H-indole (Example 4i, 20 mg, 0.071 mmol) and 4-methylphenylsulfonyl chloride (20.4 mg, 0.107 mmol). HRMS-FAB⁺ for $C_{22}H_{21}N_2O_2SF_3 \cdot HCl$, calculated MH⁺: 435.13541; found: 435.13700.

(xx) 1-Benzoyl-3-(1-methyl-1,2,3,6-tetrahydro-4-pyridinyl)indole: (9.3 mg, 25%); from 3-(1-methyl-1,2,3,6-tetrahydro-4-pyridinyl)-1H-indole (Example 4e, 25.0 mg, 0.12 mmol) and benzoyl chloride (28 uL, 0.24 mmol); HRMS-FAB⁺ for $C_{21}H_{20}N_2O$: calculated MH⁺: 317.16537; found: 317.16518.

(yy) 1-(4-Methoxybenzoyl)-3-(1-methyl-1,2,3,6-tetrahydro-4-pyridinyl)indole: (10.9 mg, 27%); from 3-(1-methyl-1,2,3,6-tetrahydro-4-pyridinyl)-1H-indole (Example 4e, 24.8 mg, 0.12 mmol) and 4-methoxybenzoyl chloride (35 uL, 0.24 mmol); HRMS-FAB⁺ for $C_{22}H_{22}N_2O_2$: calculated MH⁺: 347.17596; found: 347.17819.

(zz) 1-(4-Fluorobenzoyl)-3-(1-methyl-1,2,3,6-tetrahydro-4-pyridinyl)indole: (8.7 mg, 22%); from 3-(1-methyl-1,2,3,6-tetrahydro-4-pyridinyl)-1H-indole (Example 4e, 24.8 mg, 0.12 mmol) and 4-fluorobenzoyl chloride (28 uL, 0.24 mmol); HRMS-FAB⁺ for $C_{21}H_{19}N_2O_2F$: calculated MH⁺: 335.15598; found: 335.15560.

(aaa) 1-(2-Chlorobenzoyl)-5-cyclohexyloxy-3-(1-methyl-1,2,3,6-tetrahydro-4-pyridinyl) indole: (12.5 mg, 33%); from 5-cyclohexyloxy-3-(1-methyl-1,2,3,6-tetrahydro-4-pyridinyl)-1H-indole (Example 4c, 25.7 mg, 0.083 mmol) and 2-chlorobenzoyl chloride (25 uL, 0.20 mmol); HRMS-FAB⁺ for $C_{27}H_{29}N_2O_2Cl$: calculated MH⁺: 449.19958; found: 449.19815.

(bbb) 5-Cyclohexyloxy-1-(2,6-dichlorobenzoyl)-3-(1-methyl-1,2,3,6-tetrahydro-4-pyridinyl)indole: (40.1 mg, 100%); from 5-cyclohexyloxy-3-(1-methyl-1,2,3,6-tetrahydro-4-pyridinyl)-1H-indole (Example 4c, 25.7 mg, 0.083 mmol) and 2,6-dichlorobenzoyl chloride (30 uL, 0.21 mmol); HRMS-FAB⁺ for $C_{27}H_{28}N_2O_2Cl_2$: calculated MH⁺: 483.16061; found: 483.15611.

(ccc) 5-Cyclohexyloxy-1-(4-methoxybenzoyl)-3-(1-methyl-1,2,3,6-tetrahydro-4-pyridinyl)indole: (18.7 mg, 51%); from 5-cyclohexyloxy-3-(1-methyl-1,2,3,6-tetrahydro-4-pyridinyl)-1H-indole (Example 4c, 25.6 mg, 0.082 mmol) and 4-methoxybenzoyl chloride (30 uL, 0.20 mmol); HRMS-FAB⁺ for $C_{28}H_{32}N_2O_3$: calculated MH⁺: 445.24911; found: 445.25149.

(ddd) 5-Cyclohexyloxy-1-(3,4-methyledioxybenzoyl)-3-(1-methyl-1,2,3,6-tetrahydro-4-pyridinyl)indole: (19.0

(eee) 5-Cyclohexyloxy-1-(4-fluorobenzoyl)-3-(1-methyl-1,2,3,6-tetrahydro-4-pyridinyl)indole: (24.0 mg, 68%); from 5-cyclohexyloxy-3-(1-methyl-1,2,3,6-tetrahydro-4-pyridinyl)-1H-indole (Example 4c, 25.6 mg, 0.082 mmol) and 4-fluorobenzoyl chloride (25 uL, 0.21 mmol); HRMS-FAB$^+$ for $C_{27}H_{29}N_2O_2F$: calculated MH$^+$: 433.22913; found: 433.22733.

(fff) 1-Benzoyl-6-bromo-3-(1-methyl-1,2,3,6-tetrahydro-4-pyridinyl)indole: (23.2 mg, 68%); from 6-bromo-3-(1-methyl-1,2,3,6-tetrahydro-4-pyridinyl)-1H-indole (Example 4f, 25.0 mg, 0.086 mmol) and benzoyl chloride (20 uL, 0.17 mmol); HRMS-FAB$^+$ for $C_{21}H_{19}N_2OBr$: calculated MH$^+$: 395.07590; found: 395.07848.

(ggg) 6-Bromo-1-(4-methoxybenzoyl)-3-(1-methyl-1,2,3,6-tetrahydro-4-pyridinyl)indole: (17.4 mg, 48%); from 6-bromo-3-(1-methyl-1,2,3,6-tetrahydro-4-pyridinyl)-1H-indole (Example 4f, 25.0 mg, 0.086 mmol) and 4-methoxybenzoyl chloride (26 uL, 0.17 mmol); HRMS-FAB$^+$ for $C_{22}H_{21}O_2N_2Br$, calculated MH$^+$: 425.08646; found: 425.08292.

(hhh) 6-Bromo-1-(4-fluorobenzoyl)-3-(1-methyl-1,2,3,6-tetrahydro-4-pyridinyl)indole: (24.7 mg, 69%); from 6-bromo-3-(1-methyl-1,2,3,6-tetrahydro-4-pyridinyl)-1H-indole (Example 4f, 24.9 mg, 0.086 mmol) and 4-fluorobenzoyl chloride (20.5 uL, 0.17 mmol); HRMS-FAB$^+$ for $C_{21}H_{18}N_2OBrF$: calculated MH$^+$: 413.06647; found: 413.06465.

(iii) 5-Fluoro-3-(1-methyl-1,2,3,6-tetrahydro-4-pyridinyl)-1-(2-thiophenecarbonyl)indole: (13.5 mg, 30%), from 5-fluoro-3-(1-methyl-1,2,3,6-tetrahydro-4-pyridinyl)-1H-indole (Example 4b, 30.9 mg, 0.134 mmol) and 2-thiophenecarbonyl chloride (23.6 mg, 0.16 mmol); HRMS FAB$^+$ for $C_{19}H_{18}N_2OSF$, calculated MH$^+$: 341.11240; found: 341.11120.

(jjj) 1-Benzoyl-5-chloro-3-(1-methyl-1,2,3,6-tetrahydro-4-pyridinyl)indole hydrochloride: (20 mg, 59%) from 5-chloro-3-(1-methyl-1,2,3,6-tetrahydro-4-pyridinyl)-1H-indole (Example 4d, 25 mg, 0.1 mmol) and benzoyl chloride (21.1 mg, 0.15 mmol), m.p 256–7° C., HRMS-FAB$^+$ for $C_{21}H_{19}N_2OCl.HCl$, calculated MH$^+$(—HCl): 351.1264; found: 351.12595.

(kkk) 1-Benzoyl-3-(1-methyl-1,2,3,6-tetrahydro-4-pyridinyl)-5-trifluoromethoxyindole: (9.3 mg, 32%); from 3-(1-methyl-1,2,3,6-tetrahydro-4-pyridinyl)-5-trifluoromethoxy-1H-indole (Example 4h, 20 mg, 0.068 mmol) and benzoyl chloride (15.0 mg, 0.107 mmol); HRMS-FAB$^+$ for $C_{22}H_{19}N_2O_2F_3$, calculated MH$^+$: 401.14767; found: 401.14761.

(lll) 1-(4-Fluorobenzoyl)-3-(1-methyl-1,2,3,6-tetrahydro-4-pyridinyl)-5-trifluoromethoxyindole: (19.2 mg, 59%); from 3-(1-methyl-1,2,3,6-tetrahydro-4-pyridinyl)-5-trifluoromethoxy-1H-indole (Example 4h, 20 mg, 0.068 mmol) and 4-fluorobenzoyl chloride (17.0 mg, 0.107 mmol), HRMS-FAB$^+$ for $C_{22}H_{18}N_2O_2F_4.HCl$, calculated MH (-HCl): 419.13828; found: 419.13870.

(mmm) 1-(4-Methoxybenzoyl)-3-(1-methyl-1,2,3,6-tetrahydro-4-pyridinyl)-5-trifluoromethoxyindole: (22.2 mg, 67%); from 3-(1-methyl-1,2,3,6-tetrahydro-4-pyridinyl)-5-trifluoromethoxy-1H-indole (Example 4h, 20 mg, 0.068 mmol) and 4-methoxybenzoyl chloride (18.3 mg, 0.107 mmol), HRMS-FAB$^+$ for $C_{23}H_{21}N_2O_3F_3.HCl$, calculated MH$^+$(—HCl): 431.15826; found: 431.15694.

(nnn) 1-(2,6-Dichlorobenzoyl)-3-(1-methyl-1,2,3,6-tetrahydro-4-pyridinyl)-5-trifluoromethoxyindole: (14.3 mg, 43%); from 3-(1-methyl-1,2,3,6-tetrahydro-4-pyridinyl)-5-trifluoromethoxy-1H-indole (Example 4h, 20 mg, 0.068 mmol) and 2,6-dichlorobenzoyl chloride (22.4 mg, 0.107 mmol), HRMS-FAB$^+$ for $C_{22}H_{17}N_2O_2ClF_3$, calculated MH$^+$: 469.06973; found: 469.07199.

(ooo) 1-Benzoyl-3-(1-methyl-1,2,3,6-tetrahydro-4-pyridinyl)-5-trifluoromethylindole hydrochloride: (20.3 mg, 74%); from 3-(1-methyl-1,2,3,6-tetrahydro-4-pyridinyl)-5-trifluoromethyl-1H-indole (Example 4i, 20 mg, 0.071 mmol) and benzoyl chloride (15.0 mg, 0.107 mmol), HRMS-FAB$^+$ for $C_{22}H_{19}N_2OF_3$, calculated MH$^+$: 385.15277; found: 385.15480.

(ppp) 1-(4-Fluorobenzoyl)-3-(1-methyl-1,2,3,6-tetrahydro-4-pyridinyl)-5-trifluoromethylindole: (22.8 mg, 79%); from 3-(1-methyl-1,2,3,6-tetrahydro-4-pyridinyl)-5-trifluoromethyl-1H-indole (Example 4i, 20 mg, 0.071 mmol) and 4-fluorobenzoyl chloride (17.0 mg, 0.107 mmol), HRMS-FAB$^+$ for $C_{22}H_{18}N_2OF_4$, calculated MH$^+$(—HCl): 403.14344; found: 403.14104.

(qqq) 1-(2,6-Dichlorobenzoyl)-3-(1-methyl-1,2,3,6-tetrahydro-4-pyridinyl)-5-trifluoromethyl-indole: (25.2 mg, 78%); from 3-(1-methyl-1,2,3,6-tetrahydro-4-pyridinyl)-5-trifluoromethyl-1H-indole (Example 4i, 20 mg, 0.071 mmol) and 2,6 dichlorobenzoyl chloride (18.3 mg, 0.107 mmol), HRMS-FAB$^+$ for $C_{22}H_{18}N_2OCl_2F_3$, calculated MH$^+$(—HCl): 453.07483; found: 453.07779.

(rrr) 5-Cyclohexyloxy-1-(4-methylphenylsulfonyl)-3-(1-methyl-4-piperidinyl)indole (12.0 mg, 51%); from 5-cyclohexyloxy-3-(1-methyl-4-piperidinyl)-1H-indole (Example 5a, 15.7 mg, 0.05 mmol) and 4-methylphenylsulfonyl chloride (50 mg, 0.26 mmol); HRMS-FAB$^+$ for $C_{27}H_{34}N_2O_3S$: calculated MH$^+$: 467.23685; found: 467.23882.

(sss) 5-Chloro-3-(1-methyl-4-piperidinyl)-1-phenylsulfonylindole: (24.2 mg, 62%) from 5-chloro-3-(1-methyl-4-piperidinyl)-1H-indole (Example 5e, 25 mg, 0.1 mmol) and phenylsulfonyl chloride (26.4 mg, 0.15 mmol), HRMS-FAB$^+$ for $C_{20}H_{21}N_2O_2SCl$, calculated MH$^+$(—HCl): 389.10904; found: 389.11246.

(ttt) 5-Chloro-1-(4-fluorophenylsulfonyl )-3-(1-methyl-4-piperidinyl)indole (18.4 mg, 45%) from 5-chloro-3-(1-methyl-4-piperidinyl)-1H-indole (Example 5e, 25 mg, 0.1 mmol) and 4-fluorophenylsulfonyl chloride (29.2 mg, 0.15 mmol), HRMS-FAB$^+$ for $C_{20}H_{20}N_2O_2SClF$, calculated MH$^+$: 407.09964; found: 407.09685.

(uuu) 3-(1-Methyl-4-piperidinyl)-1-phenylsulfonylindole: (23.9 mg, 67%) from 3-(1-methyl-4-piperidinyl)-1H-indole (Example 5d, 21.5 mg, 0.1 mmol) and phenylsulfonyl chloride (26.4 mg, 0.15 mmol), HRMS-FAB$^+$ for $C_{20}H_{22}N_2O_2S$, calculated MH$^+$: 355.14807; found: 355.15074.

(vvv) 1-(4-Fluorophenylsulfonyl)-3-(1-methyl-4-piperidinyl)indole: (17.0 mg, 46%), from 3-(1-methyl-4-piperidinyl)-1H-indole (Example 5d, 21.5 mg, 0.1 mmol) and 4-fluorophenylsulfonyl chloride (29.2 mg, 0.15 mmol), HRMS-FAB$^+$ for $C_{20}H_{21}N_2O_2SF$, calculated MH$^+$: 373.13861; found: 373.13669.

(www) 6-Chloro-3-(1-methyl-4-piperidinyl)-1-phenylsulfonylindole: (35.9 mg, 92%), from 6-chloro-3-(1-methyl-4-piperidinyl)-1H-indole (Example 5b, 25 mg, 0.1 mmol) and phenylsulfonyl chloride (26.4 mg, 0.15 mmol), HRMS-FAB$^+$ for $C_{20}H_{21}N_2O_2SCl$, calculated MH$^+$: 389.10904; found: 389.11055.

(xxx) 1-(4-Fluorophenylsulfonyl)-6-chloro-3-(1-methyl-4-piperidinyl)indole: (26.8 mg, 65%), from 6-chloro-3-(1-methyl-4-piperidinyl)-1H-indole (Example 5b, 25 mg, 0.10 mmol) and 4-fluorophenylsulfonyl chloride (29.2 mg, 0.15 mmol), HRMS-FAB$^+$ for $C_{20}H_{20}N_2O_2SClF$, calculated MH$^+$: 407.09964; found: 407.09929.

(yyy) 5-Fluoro-1-phenylsulfonyl-3-(1-methyl-4-piperidinyl)indole: (27.3 mg, 73%) from 5-fluoro-3-(1-methyl-4-piperidinyl)-1H-indole (Example 5c, 25 mg, 0.1 mmol) and phenylsulfonyl chloride (26.4 mg, 0.15 mmol), HRMS-FAB$^+$ for $C_{20}H_{21}N_2O_2SF$, calculated MH$^+$: 373.13861; found: 373.13569.

(zzz) 1-(4-Fluorophenylsulfonyl)-5-fluoro-3-(1-methyl-4-piperidinyl)indole: (22.6 mg, 58%) from 5-fluoro-3-(1-methyl-4-piperidinyl)-1H-indole (Example 5c, 25 mg, 0.1 mmol) and 4-fluorophenylsulfonyl chloride (29.2 mg, 0.15 mmol), HRMS- FAB$^+$ for $C_{20}H_{20}N_2O_2SF_2$, calculated MH$^+$: 391.12918; found: 391.12926.

(ab) 1-Benzoyl-5-chloro-3-(1-methyl-4-piperidinyl)indole: (23.0 mg, 65%); from 5-chloro-3-(1-methyl-4-piperidinyl)-1H-indole (Example 5e, 25 mg, 0.10 mmol) and benzoyl chloride (21.1 mg, 0.15 mmol), HRMS-FAB$^+$ for $C_{21}H_{21}N_2OCl$, calculated MH$^+$: 353.14206; found: 353.14033.

(ac) 5-Chloro-1-(4-fluorobenzoyl)-3-(1-methyl-4-piperidinyl)indole: (22.5 mg, 61%) from 5-chloro-3-(1-methyl-4-piperidinyl)-1H-indole (Example 5e, 25 mg, 0.10 mmol) and 4-fluorobenzoyl chloride (23.8 mg, 0.15 mmol), HRMS-FAB$^+$ for $C_{21}H_{20}N_2OClF$, calculated MH$^+$: 371.13263; found: 371.13063.

(ad) 1-Benzoyl-3-(1-methyl-4-piperidinyl)indole: (28.1 mg, 88%); from 3-(1-methyl-4-piperidinyl)-1H-indole (Example 5d, 21.5 mg, 0.10 mmol) and benzoyl chloride (21.1 mg, 0.15 mmol), HRMS-FAB$^+$ for $C_{21}H_{21}N_2O$, calculated MH$^+$: 319.18103; found: 319.18293.

(ae) 1-(4-Fluorobenzoyl)-3-(1-methyl-4-piperidinyl)indole: (27.2 mg, 81%); from 3-(1-methyl-4-piperidinyl)-1H-indole (Example 5d, 21.5 mg, 0.10 mmol) and 4-fluorobenzoyl chloride (23.8 mg, 0.15 mmol), HRMS-FAB$^+$ for $C_{21}H_{21}N_2OF$, calculated MH$^+$: 337.17163; found: 337.17162.

(af) 1-Benzoyl-6-chloro-3-(1-methyl-4-piperidinyl)indole: (25.4 mg, 72%); from 6-chloro-3-(1-methyl-4-piperidinyl)-1H-indole (Example 5b, 25 mg, 0.10 mmol) and benzoyl chloride (21.1 mg, 0.15 mmol), HRMS-FAB$^+$ for $C_{21}H_{21}ClN_2O$, calculated MH$^+$: 353.14206; found: 353.13873.

(ag) 6-Chloro-1-(4-fluorobenzoyl)-3-(1-methyl-4-piperidinyl)indole: (21.8 mg, 60%); from 6-chloro-3-(1-methyl-4-piperidinyl)-1H-indole (Example 4b, 25 mg, 0.10 mmol) and 4-fluorobenzoyl chloride (23.8 mg, 0.15 mmol), HRMS-FAB$^+$ for $C_{21}H_{20}N_2OClF$, calculated MH$^+$: 371.13263; found: 371.13266.

(ah) 1-Benzoyl-5-fluoro-3-(1-methyl-4-piperidinyl)indole: (24.0 mg, 71%); from 5-fluoro-3-(1-methyl-4-piperidinyl)-1H-indole (Example 5c, 23.0 mg, 0.10 mmol) and benzoyl chloride (21.1 mg, 0.15 mmol), HRMS-FAB$^+$ for $C_{21}H_{21}N_2OF$, calculated MH$^+$: 337.17163; found: 337.16994.

(ai) 1-(4-Fluorobenzoyl)-5-fluoro-3-(1-methyl-4-piperidinyl)indole: (25.1 mg, 71%); from 5-fluoro-3-(1-methyl-4-piperidinyl)-1H-indole (Example 5c, 23.0 mg, 0.10 mmol) and 4-fluorobenzoyl chloride (23.8 mg, 0.15 mmol), HRMS-FAB$^+$ for $C_{21}H_{20}N_2OF_2$, calculated MH$^+$: 355.16220; found: 355.16313.

(aj) 5,7-Difluoro-3-(1-methyl-1,2,3,6-tetrahydro-4-pyridinyl)-1-phenylsulfonylindole: (8.5 mg, 54%); from 5,7-difluoro-3-(1-methyl- 1,2,3,6-tetrahydro-4-pyridinyl)-1H-indole (Example 4g, 10 mg, 0.04 mmol) and phenylsulfonylchloride (10.6 mg, 0.06 mmoles) with 1M NaN(TMS)$_2$ (60 μL, 0.06mmol) in THF (0.5 mL) at RT.

(ak) 5,7-Difluoro-3-(1-methyl-1,2,3,6-tetrahydro-4-pyridinyl)-1-(4-methylphenylsulfonyl)indole: (8.8 mg, 54%); from 5,7-difluoro-3-(1-methyl-1,2,3,6-tetrahydro-4-pyridinyl)-1H-indole (Example 4g, 10 mg, 0.04 mmol) and 4-methylphenylsulfonyl chloride (11.4 mg, 0.06 mmoles) with 1M NaN(TMS)$_2$ (60 μL, 0.06 mmol) in THF (0.5 mL) at RT.

(al) 5,7-Difluoro-1-(4-fluorophenylsulfonyl)-3-(1-methyl-1,2,3,6-tetrahydro-4-pyridinyl)indole: (7.6 mg, 46.4%); from 5,7-difluoro-3-(1-methyl-1,2,3,6-tetrahydro-4-pyridinyl)-1H-indole (Example 4g, 10 mg, 0.04 mmol) and 4-fluorophenylsulfonyl chloride (11.7 mg, 0.06 mmol) with 1M NaN(TMS)$_2$ (60 μL, 0.06 mmoles) in THF (0.5 mL) at RT.

(am) 1-(4-Bromophenylsulfonyl)-5,7-difluoro-3-(1-methyl-1,2,3,6-tetrahydro-4-pyridinyl)indole: (8.7 mg, 48%); from 5,7-difluoro-3-(1-methyl-1,2,3,6-tetrahydro-4-pyridinyl)-1H-indole (Example 4g, 10 mg, 0.04 mmol) and 4-bromophenylsulfonyl chloride (15.3 mg, 0.06 mmol) with 1M NaN(TMS)$_2$ (60 μL, 0.06 mmol) in THF (0.5 mL) at RT.

(an) 1-(4-Chlorophenylsulfonyl)-5,7-difluoro-3-(1-methyl-1,2,3,6-tetrahydro-4-pyridinyl)indole: (6.7mg, 39%); from 5,7-difluoro-3-(1-methyl-1,2,3,6-tetrahydro-4-pyridinyl)-1H-indole (Example 4g, 10 mg, 0.04mmol) and 4-chlorophenylsulfonyl chloride (12.7 mg, 0.06 mmoles) with 1M NaN(TMS)$_2$ (60 μL, 0.06 mmol) in THF (0.5 mL) at RT.

(ao) 5,7-Difluoro-3-(1-methyl-1,2,3,6-tetrahydro-4-pyridinyl)-1-(1-naphthylsulfonyl)indole: (9.2 mg, 52%); from 5,7-difluoro-3-(1-methyl-1,2,3,6-tetrahydro-4-pyridinyl)-1H-indole (Example 4g, 10 mg, 0.04 mmol) and 1-naphthalenesulfonyl chloride (13.6 mg, 0.06 mmol) with 1M NaN(TMS)$_2$ (60 μL, 0.06 mmol) in THF (0.5 mL) at RT.

(ap) 5,7-Difluoro-3-(1-methyl-1,2,3,6-tetrahydro-4-pyridinyl)-1-(2-naphthylsulfonyl)indole: (5.1 mg, 29%); from 5,7-difluoro-3-(1-methyl-1,2,3,6-tetrahydro-4-pyridinyl)-1H-indole (Example 4g, 10 mg, 0.04 mmol) and 2-naphthalenesulfonyl chloride (13.6 mg, 0.06 mmol) with 1M NaN(TMS)$_2$ (60 μL, 0.06 mmol) in THF (0.5 mL) at RT.

(aq) 5,7-Difluoro-3-(1-methyl-1,2,3,6-tetrahydro-4-pyridinyl)-1-(2,4,6-trimethylphenyl)sulfonylindole: (5.7 mg, 33%); from 5,7-difluoro-3-(1-methyl-1,2,3,6-tetrahydro-4-pyridinyl)-1H-indole (Example 4g, 10 mg, 0.04 mmol) and 2,4,6-trimethylphenylsulfonyl chloride (13.1 mg, 0.06 mmol) with 1M NaN(TMS)$_2$ (60 μL, 0.06 mmol) in THF (0.5 mL).

(ar) 5,7-Difluoro-1-(4-fluorobenzoyl)-3-(1-methyl-1,2,3,6-tetrahydro-4-pyridinyl)indole: (6.3 mg, 42%); from 5,7-difluoro-3-(1-methyl-1,2,3,6-tetrahydro-4-pyridinyl)-1H-indole (Example 4g, 10 mg, 0.04 mmol) and 4-fluorobenzoyl chloride (9.5 mg, 0.06 mmol) with 1M NaN(TMS)$_2$ (60 µL, 0.06 mmol) in THF (0.5 mL) at RT.

(as) 1-(2,5-Dichlorobenzoyl)-5,7-difluoro-3-(1-methyl-1,2,3,6-tetrahydro-4-pyridinyl)indole: (5.6 mg, 33%); from 5,7-difluoro-3-(1-methyl-1,2,3,6-tetrahydro-4-pyridinyl)-1H-indole (Example 4g, 10 mg, 0.04 mmol) and 2,5-dichlorobenzoyl chloride (12.6 mg, 0.06 mmol) with 1M NaN(TMS)$_2$ (60 µL, 0.06 mmol) in THF (0.5 mL) at RT.

Example 8

1-Benzoyl-3-(1-methyl-1,2,3,6-tetrahydro-4-pyridinyl)-5-vinylindole

Tributylvinylstannane was added to a solution of 1-benzoyl-5-bromo-3-(1-methyl-1,2,3,6-tetrahydro-4-pyridinyl)indole (Example 6g) in DMF and the reaction mixture was heated to 100° C. overnight. The mixture was partitioned between ethyl acetate and water, sequentially washed with water and brine, and dried over sodium carbonate. Flash chromatography (silica gel, 5% 2M methanolic ammonia in dichloromethane) yielded 1-benzoyl-3-(1-methyl-1,2,3,6-tetrahydro-4-pyridinyl)-5-vinylindole.

Example 13

Binding Affinity for the 5-HT$_6$ Receptor

All of the compounds of the invention were evaluated using cell types receptive specifically to the 5-HT$_6$ receptor (for cloning and characterization of the human 5-HT$_6$ receptor see Kohen, et al. J. Neurochemistry, 66, 1996: 47–56). The assay protocol generally entailed the incubation of membranes prepared from cells expressing the 5-HT$_6$ receptor with $^3$H-LSD. Increasing levels of the test compound were incubated with the radioligand and the membrane homogenates prepared from the recombinant cells. After a 60 minute incubation at 37° C., the incubation was terminated by vacuum filtration. The filters were washed with buffer and the filters were counted for radioactivity using liquid scintillation spectrometry. The affinity of the test compound for the 5-HT$_6$ receptor was determined by computer-assisted analysis of the data and determining the amount of the compound necessary to inhibit 50% of the binding of the radioligand to the receptor. Concentrations ranging from $10^{-11}$ M to $10^{-5}$ M of the test compound were evaluated. For comparison, the affinity of clozapine for the 5-HT$_6$ receptor (Ki ~3 nm) was used as a standard. All of the compounds of the invention exhibited affinity for the human 5-HT$_6$ receptor, with Ki's of not greater than 1000 nM. Preferred compounds, those of examples 6b, 6c, 6f, 6g, 7a, 7b, 7c, 7d, 7e, 7f, 7g, 7i, 7j, 7l, 7m, 7bb, 7cc, 7dd, 7gg, 7ii, 7jj, 7kk, 7oo, 7pp, 7rr, 7vv, 7ww, 7aaa, 7jjj, 7qqq, 7uuu, 7aj, 7ak, 7am, 7an, 7ao, 7ap, 7ar and 7as, exhibited Ki's of not greater than 50 nM. Particularly preferred compounds, those of examples 6b, 6c, 6f, 7a, 7c, 7bb, 7cc, 7dd, 7gg, 7ii, 7jj, 7kk, 7oo, 7pp, 7rr, 7aaa, 7aj, 7ak, 7am, 7an, 7ao, 7ap and 7ar, exhibited Ki's of not greater than 5 nM. The compounds of the invention also bound to the human 5-HT$_6$ receptor in a selective manner, relative to the human 5-HT$_{2c}$ and 5-HT$_7$ receptors. That is, the compounds of the invention bound to the human 5-HT$_6$ receptor with at least a 2-fold greater affinity, relative to the human 5-HT$_{2c}$ and 5-HT$_7$ receptors. Preferred compounds, for example, those of examples 6b, 6g, 7i, 7m, 7bb, 7dd, 7gg, 7hh, and 7ii, bound to the human 5-HT$_6$ receptor with at least a 60-fold greater affinity, relative to the human 5-HT$_{2c}$ and 5-HT$_7$ receptors. More preferred compounds, for example, those of examples 7m, 7gg and 7ii, bound to the human 5-HT$_6$ receptor with at least a 300-fold greater affinity, relative to the human 5-HT$_{2c}$ and 5-HT$_7$ receptors.

Example 14

Effect of Compounds on the cAMP Response of Human 5-HT$_6$ Receptors

The antagonist (or agonist) property of compounds for human 5-HT$_6$ receptors was determined by testing their effect on cAMP accumulation in stably transfected HEK293 cells.

Binding of an agonist to the human 5-HT$_6$ receptor will lead to a increase in adenyl cyclase activity. A compound which is an agonist will show an increase in cAMP production and a compound which is an antagonist will block the agonist effect.

Cell Assay:

Human 5-HT$_6$ receptors were cloned and stably expressed in HEK293 cells. These cells were plated in 6 well plates in DMEM/F12 media with 10% fetal calf serum (FCS) and 500 µg/mL G418 and incubated at 37° C. in a CO$_2$ incubator. The cells were allowed to grow to about 70% confluence before initiation of the experiment.

On the day of the experiment, the culture media was removed, and the cells were washed once with serum free medium (SFM). Two mL of SFM+IBMX media was added and incubated at 37° C. for 10 min. The media were removed and fresh SFM+IBMX media containing various compounds, and 1 µM serotonin (as antagonist) were added to the appropriate wells and incubated for 30 min. Following incubation, the media were removed and the cells were washed once with 1 mL of PBS (phosphate buffered saline). Each well was treated with 1 mL cold 95% ethanol and 5 mM EDTA (2:1) at 4° C. for 1 hour. The cells were then scraped and transferred into Eppendorf tubes. The tubes were centrifuged for 5 min at 4° C., and the supernatants were stored at 4° C. until assayed.

cAMP Measurement:

cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites on anti-cAMP antibody. The antibody is immobilized onto polystyrene microtitre wells precoated with a second antibody. The reaction is started by adding 50 µL peroxidase-labeled cAMP to the sample (100 µL) preincubated with the antiserum (100 µL) for 2 hours at 4° C. Following 1 hour incubation at 4° C., the unbound ligand is separated by a simple washing procedure. Then an enzyme substrate, tetramethylbenzidine (TMB), is added and incubated at room temperature for 60 min. The reaction is stopped by the addition of 100 µL 1.0 M sulfuric acid and the resultant color read by a microtitre plate spectrophotometer at 450 nM within 30 minutes.

All of the compounds of the invention which were tested in the above assays were found to be antagonists. The potency of compounds of the invention as antagonists is expressed as an EC$_{50}$, which is the concentration causing 50% inhibition of the serotonin-stimulated cAMP response. The table below presents the EC$_{50}$'s of some of the compounds of the invention compared to clozapine as a reference compound.

| Example # | EC$_{50}$ (M) |
|---|---|
| clozapine | 9.5 × 10$^{-9}$ |
| 6 cc | 1.0 × 10$^{-8}$ |
| 5b | 1.9 × 10$^{-6}$ |

We claim:

1. A compound according to formula I and salts, solvates, and hydrates thereof:

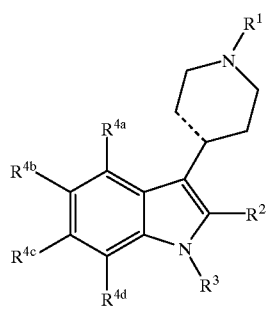

I wherein:
- R$^1$ is selected from the group consisting of H and C$_{1-4}$ alkyl;
- R$^2$ is selected from the group consisting of H, C$_{1-4}$ alkyl and benzyl;
- — — — represents a single or double bond;
- R$^3$ is SO$_2$R$^5$;
- R$^{4a}$ is selected from the group consisting of H, OH, halo, C$_{1-4}$ alkyl and C$_{1-4}$akloxy;
- R$^{4b}$ is selected from the group consisting of H, hydroxy, halo, C$_{3-7}$ cycloalkyloxy, C$_{1-4}$ alky, benzyloxy, phenoxy, trifluoromethyl, trifluoromethoxy, and vinyl;
- R$^{4c}$ is selected from the group consisting of H, OH, halo, C$_{1-4}$ alkyl and C$_{1-4}$alkoxy;
- R$^{4d}$ is selected from the group consisting of H, OH halo, C$_{1-4}$ alkyl and C$_{1-4}$alkoxy; and
- R$^5$ is selected from the group consisting of phenyl, pyridyl, thienyl, quinolinyl and naphthyl which are optionally substituted with 1–4 substituents selected from C$_{1-4}$alkoxy, C$_{1-4}$alkyl, halo, nitro, trifluoromethyl, trifluoromethoxy, 1,2-methylenedioxy, C$_{1-4}$alkylcarbonyl, C$_{1-4}$alkoxycarbonyl and C$_{1-4}$alkylS—.

2. A compound according to claim 1, wherein R$^1$ is methyl.

3. A compound according to claim 1, wherein R$^2$ is H.

4. A compound according to claim 1, wherein R$^5$ is selected from the group consisting of phenyl, napthyl and thienyl which are all optionally substituted with 1–3 groups selected independently from methyl, methoxy, halo, trifluoromethyl and 1,2-methylenedioxy.

5. A compound according to claim 4, wherein R$^5$ is selected from the group consisting of naphthyl and phenyl optionally substituted with 1–3 substituents independently selected from chloro, bromo, fluoro, nitro, methyl and methoxy.

6. A compound according to claim 5, wherein R$^5$ is selected from the group consisting of phenyl, 2-chlorophenyl, 2-bromophenyl, 1-naphthyl, 4-fluorophenyl, 4-chlorophenyl, 4-bromophenyl, 2,4-dichlorophenyl, 3-nitro-4-chlorophenyl, 2,4,6-trimethylphenyl, 4-methyoxyphenyl and 4-methylphenyl.

7. A compound according to claim 1, wherein R$^{4a}$, R$^{4c}$ and R$^{4d}$ are H and R$^{4b}$ is selected from H, halo, methyl, trifluoromethyl and methoxy.

8. A compound according to claim 1, wherein R$^{4b}$ and R$^{4d}$ are halo.

9. A compound according to claim 1, wherein — — — represents a double bond.

10. The compound of claim 1, wherein:
- R$^1$ is C$_{1-4}$ alkyl;
- R$^2$ is selected from the group consisting of H, C$_{1-4}$ alkyl and benzyl;
- — — — represents a double bond;
- R$^3$ is SO$_2$R$^5$;
- R$^{4a}$ is H;
- R$^{4b}$ is selected from the group consisting of H, halo, C$_{3-7}$ cycloalkyloxy, trifluoromethyl, and trifluoromethoxy;
- R$^{4c}$ is selected from the group consisting of H, halo;
- R$^{4d}$ is selected from the group consisting of H, and halo; and
- R$^5$ is selected from the group consisting of phenyl and naphthyl which is optionally substituted with 1–4 substituents selected from C$_{1-4}$alkoxy, C$_{1-4}$alkyl, halo, and nitro.

11. The compound of claim 1, wherein:
- R$^1$ is C$_{1-4}$alkyl;
- R$^2$ is selected from the group consisting of H, C$_{1-4}$alkyl and benzyl;
- — — — represents a single or double bond;
- R$^3$ is SO$_2$R$^5$;
- R$^{4a}$ is selected from the group consisting of H, OH, halo, C$_{1-4}$alkyl and C$_{1-4}$alkoxy;
- R$^{4b}$ is selected from the group consisting of H, hydroxy, halo, C$_{3-7}$ cycloalkyloxy, C$_{1-4}$alkoxy, C$_{1-4}$alkyl, benzyloxy, phenoxy, trifluoromethyl, and trifluoromethoxy and vinyl;
- R$^{4c}$ is selected from the group consisting of H, OH, halo, C$_{1-4}$alkyl and C$_{1-4}$alkoxy;
- R$^{4d}$ is selected from the group consisting Of H, OH, and halo, C$_{1-4}$alkyl and C$_{1-4}$alkoxy; and
- R$^5$ is selected from the group consisting of phenyl, pyridyl, thienyl, quinolinyl and naphthyl which is optionally substituted with 1–4 substituents selected from C$_{1-4}$alkoxy, C$_{1-4}$alkyl, halo, and nitro, trifluoromethyl, trifluoromethoxy, 1,2-methylenedioxy, C$_{1-4}$alkylcarbonyl, C$_{1-4}$alkoxycarbonyl and C$_{1-4}$alkylS—.

12. A compound according to claim 1, wherein R$^1$ is hydrogen.

13. A compound according to claim 1, which is selected from:
- 3-(1-Methyl-1,2,3,6-tetrahydro-4-pyridinyl)-1-phenylsulfonylindole;
- 1-(4-Methoxyphenylsulfonyl)-3-(1-methyl-1,2,3,6-tetrahydro-4-pyridinyl)indole;
- 1-(4-Fluorophenylsulfonyl)-3-(1-methyl-1,2,3,6-tetrahydro-4-pyridinyl)indole;
- 1-(4-Bromophenylsulfonyl)-5-fluoro-3-(1-methyl-1,2,3,6-tetrahydro-4-pyridinyl)indole;
- 5-Fluoro-1-(2,5-dichlorophenylsulfonyl)-3-(1-methyl-1,2,3,6-tetrahydro-4-pyridinyl)indole;

1-(4-Chloro-3-nitrophenylsulfonyl)-5-fluoro-3-(1-methyl-1,2,3,6-tetrahydro-4-pyridinyl)indole;

5-Fluoro-3-(1-methyl-1,2,3,6-tetrahydro-4-pyridinyl)-1-(2,4,6-trimethylphenylsulfonyl)indole;

5-Fluoro-3-(1-methyl-1,2,3,6-tetrahydro-4-pyridinyl)-1-(2,4,6-triisopropylphenylsulfonyl)indole;

5-Cyclohexyloxy-1-(4-methylphenylsulfonyl)-3-(1-methyl-1,2,3,6-tetrahydro-4-pyridinyl)indole;

6-Bromo-3-(1-methyl-1,2,3,6-tetrahydro-4-pyridinyl)-1-phenylsulfonylindole;

6-Bromo-1-(4-methoxyphenylsulfonyl)-3-(1-methyl-1,2,3,6-tetrahydro-4-pyridinyl)indole;

6-Bromo-1-(4-fluorophenylsulfonyl)-3-(1-methyl-1,2,3,6-tetrahydro-4-pyridinyl)indole;

5-Cyclohexyloxy-3-(1-methyl-1,2,3,6-tetrahydro-4-pyridinyl)-1-phenylsulfonylindole;

5-Cyclohexyloxy-3-(1-methyl-1,2,3,6-tetrahydro-4-pyridinyl)-1-(1-naphthylsulfonyl)indole;

5-Cyclohexyloxy-3-(1-methyl-1,2,3,6-tetrahydro-4-pyridinyl)-1-(2-naphthylsulfonyl)indole;

1-(2-Bromophenylsulfonyl)-5-cyclohexyloxy-3-(1-methyl-1,2,3,6-tetrahydro-4-pyridinyl)indole;

5-Cyclohexyloxy-1-(2,5-dichlorophenylsulfonyl)-3-(1-methyl-1,2,3,6-tetrahydro-4-pyridinyl)indole;

5-Cyclohexyloxy-3-(1-methyl-1,2,3,6-tetrahydro-4-pyridinyl)-1-(2,4,6-trimethylphenylsulfonyl)indole;

5-Cyclohexyloxy-3-(1-methyl-1,2,3,6-tetrahydro-4-pyridinyl)-1-(2,4,6-triisopropylphenylsulfonyl)indole;

5-Cyclohexyloxy-3-(1-methyl-1,2,3,6-tetrahydro-4-pyridinyl)-1-(3-nitrophenylsulfonyl)indole;

1-(4-Chloro-3-nitrophenylsulfonyl)-5-cyclohexyloxy-3-(1-methyl-1,2,3,6-tetrahydro-4-pyridinyl)indole;

5-Cyclohexyloxy-3-(1-methyl-1,2,3,6-tetrahydro-4-pyridinyl)-1-(3-nitro-4-trifluoromethylphenylsulfonyl)indole;

1-(4-Bromophenylsulfonyl)-5-cyclohexyloxy-3-(1-methyl-1,2,3,6-tetrahydro-4-pyridinyl)indole;

5-Cyclohexyloxy-1-(4-methoxyphenylsulfonyl)-3-(1-methyl-1,2,3,6-tetrahydro-4-pyridinyl)indole;

5-Cyclohexyloxy-1-(4-fluorophenylsulfonyl)-3-(1-methyl-1,2,3,6-tetrahydro-4-pyridinyl)indole;

1-(4-Chlorophenylsulfonyl)-5-cyclohexyloxy-3-(1-methyl-1,2,3,6-tetrahydro-4-pyridinyl)indole;

1-(4-t-Butylphenylsulfonyl)-5-cyclohexyloxy-3-(1-methyl-1,2,3,6-tetrahydro-4-pyridinyl)indole;

1-(2-Bromophenylsulfonyl)-5-fluoro-3-(1-methyl-1,2,3,6-tetrahydro-4-pyridinyl)indole;

1-(4-Fluorophenylsulfonyl)-5-fluoro-3-(1-methyl-1,2,3,6-tetrahydro-4-pyridinyl)indole;

1-(4-Chlorophenylsulfonyl)-5-fluoro-3-(1-methyl-1,2,3,6-tetrahydro-4-pyridinyl)indole;

1-(4-t-Butylphenylsulfonyl)-4-fluoro-3-(1-methyl-1,2,3,6-tetrahydro-4-pyridinyl)indole;

5-Fluoro-3-(1-methyl-1,2,3,6-tetrahydro-4-pyridinyl)-1-(3-nitrophenylsulfonyl)indole;

5-Fluoro-3-(1-methyl-1,2,3,6-tetrahydro-4-pyridinyl)-1-(1-naphthylsulfonyl)indole;

5-Fluoro-3-(1-methyl-1,2,3,6-tetrahydro-4-pyridinyl)-1-(2-naphthylsulfonyl)indole;

5-Fluoro-3-(1-methyl-1,2,3,6-tetrahydro-4-pyridinyl)-1-phenylsulfonylindole;

5-Chloro-3-(1-methyl-1,2,3,6-tetrahydro-4-pyridinyl)-1-phenylsulfonylindole;

5-Chloro-1-(4-fluorophenylsulfonyl)-3-(1-methyl-1,2,3,6-tetrahydro-4-pyridinyl)indole;

3-(1-Methyl-1,2,3,6-tetrahydro-4-pyridinyl)-1-phenylsulfonyl-5-trifluoromethoxyindole;

1-(4-Fluorophenylsulfonyl)-3-(1-methyl-1,2,3,6-tetrahydro-4-pyridinyl)-5-trifluoromethoxyindole;

1-(4-t-Butylphenylsulfonyl)-3-(1-methyl-1,2,3,6-tetrahydro-4-pyridinyl)-5-trifluoromethoxyindole;

1-(4-Chlorophenylsulfonyl)-3-(1-methyl-1,2,3,6-tetrahydro-4-pyridinyl)-5-trifluoromethoxyindole;

1-(4-Methylphenylsulfonyl)-3-(1-methyl-1,2,3,6-tetrahydro-4-pyridinyl)-5-trifluoromethoxyindole;

(4-Methoxyphenylsulfonyl)-3-(1-methyl-1,2,3,6-tetrahydro-4-pyridinyl)-5-trifluoromethoxyindole;

3-(1-Methyl-1,2,3,6-tetrahydro-4-pyridinyl)-1-phenylsulfonyl-5-trifluoromethylindole hydrochloride;

1-(4-Fluorophenylsulfonyl)-3-(1-methyl-1,2,3,6-tetrahydro-4-pyridinyl)-5-trifluoromethylindole hydrochloride;

1-(4-t-Butylphenylsulfonyl)-3-(1-methyl-1,2,3,6-tetrahydro-4-pyridinyl)-5-trifluoromethylindole hydrochloride;

1-(4-Chlorophenylsulfonyl)-3-(1-methyl-1,2,3,6-tetrahydro-4-pyridinyl)-5-trifluoromethylindole hydrochloride;

1-(4-Methoxyphenylsulfonyl)-3-(1-methyl-1,2,3,6-tetrahydro-4-pyridinyl)-5-trifluoromethylindole hydrochloride;

1-(4-Methylphenylsulfonyl)-3-(1-methyl-1,2,3,6-tetrahydro-4-pyridinyl)-5-trifluoromethylindole hydrochloride;

5-Cyclohexyloxy-1-(4-methylphenylsulfonyl)-3-(1-methyl-4-piperidinyl)indole;

5-Chloro-3-(1-methyl-4-piperidinyl)-1-phenylsulfonylindole;

5-Chloro-1-(4-fluorophenylsulfonyl)-3-(1-methyl-4-piperidinyl)indole;

3-(1-Methyl-4-piperidinyl)-1-phenylsulfonylindole;

1-(4-Fluorophenylsulfonyl)-3-(1-methyl-4-piperidinyl)indole;

6-Chloro-3-(1-methyl-4-piperidinyl)-1-phenylsulfonylindole;

1-(4-Fluorophenylsulfonyl)-6-chloro-3-(1-methyl-4-piperidinyl)indole;

5-Fluoro-1-phenylsulfonyl-3-(1-methyl-4-piperidinyl)indole;

1-(4-Fluorophenylsulfonyl)-5-fluoro-3-(1-methyl-4-piperidinyl)indole 5,7-Difluoro-3-(1-methyl-1,2,3,6-tetrahydro-4-pyridinyl)-1-phenylsulfonylindole;

5,7-Difluoro-3-(1-methyl-1,2,3,6-tetrahydro-4-pyridinyl)-1-(4-methylphenylsulfonyl)indole;

5,7-Difluoro-1-(4-fluorophenylsulfonyl)-3-(1-methyl-1,2,3,6-tetrahydro-4-pyridinyl)indole;

1-(4-Bromophenylsulfonyl)-5,7-difluoro-3-(1-methyl-1,2,3,6-tetrahydro-4-pyridinyl)indole;

1-(4-Chlorophenylsulfonyl)-5,7-difluoro-3-(1-methyl-1,2,3,6-tetrahydro-4-pyridinyl)indole;

5,7-Difluoro-3-(1-methyl-1,2,3,6-tetrahydro-4-pyridinyl)-1-(1-naphthylsulfonyl)indole;

5,7-Difluoro-3-(1-methyl-1,2,3,6-tetrahydro-4-pyridinyl)-1-(2-naphthylsulfonyl)indole; and 5,7-Difluoro-3-(1-methyl-1,2,3,6-tetrahydro-4-pyridinyl)-1-(2,4,6-trimethylphenyl)sulfonylindole.

14. A compound according to claim 1, which is selected from the group consisting of:

5-Fluoro-1-(4-methylphenylsulfonyl)-3-(1-methyl-1,2,3,6-tetrahydro-4-pyridinyl)indole;
3-(1-Methyl-1,2,3,6-tetrahydro-4-pyridinyl)-1-phenylsulfonylindole;
1-(4-Methoxyphenylsulfonyl)-3-(1-methyl-1,2,3,6-tetrahydro-4-pyridinyl)indole;
1-(4-Fluorophenylsulfonyl)-3-(1-methyl-1,2,3,6-tetrahydro-4-pyridinyl)indole;
1-(4-Bromophenylsulfonyl)-5-fluoro-3-(1-methyl-1,2,3,6-tetrahydro-4-pyridinyl)indole;
5-Fluoro-1-(2,5-dichlorophenylsulfonyl)-3-(1-methyl-1,2,3,6-tetrahydro-4-pyridinyl)indole;
1-(4-Chloro-3-nitrophenylsulfonyl)-5-fluoro-3-(1-methyl-1,2,3,6-tetrahydro-4-pyridinyl)indole;
5-Fluoro-3-(1-methyl-1,2,3,6-tetrahydro-4-pyridinyl)-1-(2,4,6-trimethylphenylsulfonyl)indole;
5-Cyclohexyloxy-1-(4-methylphenylsulfonyl)-3-(1-methyl-1,2,3,6-tetrahydro-4-pyridinyl)indole;
6-Bromo-3-(1-methyl-1,2,3,6-tetrahydro-4-pyridinyl)-1-phenylsulfonylindole;
6-Bromo-1-(4-fluorophenylsulfonyl)-3-(1-methyl-1,2,3,6-tetrahydro-4-pyridinyl)indole;
5-Cyclohexyloxy-3-(1-methyl-1,2,3,6-tetrahydro-4-pyridinyl)-1-phenylsulfonylindole;
5-Cyclohexyloxy-3-(1-methyl-1,2,3,6-tetrahydro-4-pyridinyl)-1-(1-naphthylsulfonyl)indole;
5-Cyclohexyloxy-3-(1-methyl-1,2,3,6-tetrahydro-4-pyridinyl)-1-(2-naphthylsulfonyl)indole;
1-(2-Bromophenylsulfonyl)-5-cyclohexyloxy-3-(1-methyl-1,2,3,6-tetrahydro-4-pyridinyl)indole;
5-Cyclohexyloxy-1-(4-methoxyphenylsulfonyl)-3-(1-methyl-1,2,3,6-tetrahydro-4-pyridinyl)indole;
1-(2-Bromophenylsulfonyl)-5-fluoro-3-(1-methyl-1,2,3,6-tetrahydro-4-pyridinyl)indole;
1-(4-Fluorophenylsulfonyl)-5-fluoro-3-(1-methyl-1,2,3,6-tetrahydro-4-pyridinyl)indole;
1-(4-Chlorophenylsulfonyl)-5-fluoro-3-(1-methyl-1,2,3,6-tetrahydro-4-pyridinyl)indole;
5-Fluoro-3-(1-methyl-1,2,3,6-tetrahydro-4-pyridinyl)-1-(3-nitrophenylsulfonyl)indole;
5-Fluoro-3-(1-methyl-1,2,3,6-tetrahydro-4-pyridinyl)-1-(1-naphthylsulfonyl)indole;
5-Fluoro-3-(1-methyl-1,2,3,6-tetrahydro-4-pyridinyl)-1-(2-naphthylsulfonyl)indole;
5-Fluoro-3-(1-methyl-1,2,3,6-tetrahydro-4-pyridinyl)-1-phenylsulfonylindole;
5-Chloro-3-(1-methyl-1,2,3,6-tetrahydro-4-pyridinyl)-1-phenylsulfonylindole;
5-Chloro-1-(4-Fluorophenylsulfonyl)-3-(1-methyl-1,2,3,6-tetrahydro-4-pyridinyl)indole;
1-(4-Chlorophenylsulfonyl)-3-(1-methyl-1,2,3,6-tetrahydro-4-pyridinyl)-5-trifluoromethoxyindole;
1-(4-Methylphenylsulfonyl)-3-(1-methyl-1,2,3,6-tetrahydro-4-pyridinyl)-5-trifluoromethoxyindole;
3-(1-Methyl-1,2,3,6-tetrahydro-4-pyridinyl)-1-phenylsulfonyl-5-trifluoromethylindole hydrochloride;
1-(4-Chlorophenylsulfonyl)-3-(1-methyl-1,2,3,6-tetrahydro-4-pyridinyl)-5-trifluoromethylindole hydrochloride;
1-(4-Methoxyphenylsulfonyl)-3-(1-methyl-1,2,3,6-tetrahydro-4-pyridinyl)-5-trifluoromethylindole hydrochloride;
1-(4-Methylphenylsulfonyl)-3-(1-methyl-1,2,3,6-tetrahydro-4-pyridinyl)-5-trifluoromethylindole hydrochloride;
3-(1-Methyl-4-piperidinyl)-1-phenylsulfonylindole;
6-Chloro-3-(1-methyl-4-piperidinyl)-1-phenylsulfonylindole;
5,7-Difluoro-3-(1-methyl-1,2,3,6-tetrahydro-4-pyridinyl)-1-phenylsulfonylindole;
5,7-Difluoro-3-(1-methyl-1,2,3,6-tetrahydro-4-pyridinyl)-1-(4-methylphenylsulfonyl)indole;
1-(4-Bromophenylsulfonyl)-5,7-difluoro-3-(1-methyl-1,2,3,6-tetrahydro-4-pyridinyl)indole;
1-(4-Chlorophenylsulfonyl)-5,7-difluoro-3-(1-methyl-1,2,3,6-tetrahydro-4-pyridinyl)indole;
5,7-Difluoro-3-(1-methyl-1,2,3,6-tetrahydro-4-pyridinyl)-1-(2-naphthylsulfonyl)indole; and
5,7-Difluoro-3-(1-methyl-1,2,3,6-tetrahydro-4-pyridinyl)-1-(1-naphthylsulfonyl)indole.

15. A compound according to claim 1, which is selected from the group consisting of:

5-Fluoro-1-(4-methylphenylsulfonyl)-3-(1-methyl-1,2,3,6-tetrahydro-4-pyridinyl)indole;
3-(1-Methyl-1,2,3,6-tetrahydro-4-pyridinyl)-1-phenylsulfonylindole;
1-(4-Fluorophenylsulfonyl)-3-(1-methyl-1,2,3,6-tetrahydro-4-pyridinyl)indole;
1-(2-Bromophenylsulfonyl)-5-fluoro-3-(1-methyl-1,2,3,6-tetrahydro-4-pyridinyl)indole;
1-(4-Fluorophenylsulfonyl)-5-fluoro-3-(1-methyl-1,2,3,6-tetrahydro-4-pyridinyl)indole;
1-(4-Chlorophenylsulfonyl)-5-fluoro-3-(1-methyl-1,2,3,6-tetrahydro-4-pyridinyl)indole;
5-Fluoro-3-(1-methyl-1,2,3,6-tetrahydro-4-pyridinyl)-1-(1-naphthylsulfonyl)indole;
5-Fluoro-3-(1-methyl-1,2,3,6-tetrahydro-4-pyridinyl)-1-phenylsulfonylindole;
5-Chloro-3-(1-methyl-1,2,3,6-tetrahydro-4-pyridinyl)-1-phenylsulfonylindole;
5-Chloro-1-(4-fluorophenylsulfonyl)-3-(1-methyl-1,2,3,6-tetrahydro-4-pyridinyl)indole;
1-(4-Chlorophenylsulfonyl)-3-(1-methyl-1,2,3,6-tetrahydro-4-pyridinyl)-5-trifluoromethoxyindole;
1-(4-Methylphenylsulfonyl)-3-(1-methyl-1,2,3,6-tetrahydro-4-pyridinyl)-5-trifluoromethoxyindole;
3-(1-Methyl-1,2,3,6-tetrahydro-4-pyridinyl)-1-phenylsulfonyl-5-trifluoromethylindole hydrochloride;
5,7-Difluoro-3-(1-methyl-1,2,3,6-tetrahydro-4-pyridinyl)-1-phenylsulfonylindole;
5,7-Difluoro-3-(1-methyl-1,2,3,6-tetrahydro-4-pyridinyl)-1-(4-methylphenylsulfonyl)indole;
1-(4-Bromophenylsulfonyl)-5,7-difluoro-3-(1-methyl-1,2,3,6-tetrahydro-4-pyridinyl)indole;
1-(4-Chlorophenylsulfonyl)-5,7-difluoro-3-(1-methyl-1,2,3,6-tetrahydro-4-pyridinyl)indole;
5,7-Difluoro-3-(1-methyl-1,2,3,6-tetrahydro-4-pyridinyl)-1-(1-naphthylsulfonyl)indole; and
5,7-Difluoro-3-(1-methyl-1,2,3,6-tetrahydro-4-pyridinyl)-1-(2-naphthylsulfonyl)indole.

16. A pharmaceutical composition, comprising a pharmaceutically acceptable carrier and, in an amount effective to antagonize the 5-HT$_6$ receptor, a compound of claim 1.

17. A pharmaceutical composition, comprising a pharmaceutically acceptable carrier and, in an amount effective to antagonize the 5-$HT_6$ receptor, a compound of according to claim 13.

18. A method for treating a patient having a medical condition for which a 5-$HT_6$ receptor antagonist is needed, comprising the step of administering to the patient a pharmaceutical composition as defined in claim 16.

19. A method for treating a patient according to claim 18, wherein the medical condition is schizophrenia.

* * * * *